(12) United States Patent
Oharuda et al.

(10) Patent No.: US 11,684,693 B2
(45) Date of Patent: Jun. 27, 2023

(54) CELL OR TISSUE EMBEDDING DEVICE

(71) Applicants: Japan Vam & Poval Co., Ltd., Osaka (JP); National University Corporation Tohoku University, Sendai (JP)

(72) Inventors: Akinobu Oharuda, Osaka (JP); Yoshihiro Kimura, Osaka (JP); Masafumi Goto, Sendai (JP)

(73) Assignees: Japan Vam & Poval Co., Ltd., Sakai (JP); National University Corporation Tohoku University, Sendai (JP)

( * ) Notice: Subject to any disclaimer, the term of this patent is extended or adjusted under 35 U.S.C. 154(b) by 0 days.

(21) Appl. No.: 16/487,400

(22) PCT Filed: Feb. 23, 2018

(86) PCT No.: PCT/JP2018/006661
§ 371 (c)(1),
(2) Date: Aug. 20, 2019

(87) PCT Pub. No.: WO2018/155621
PCT Pub. Date: Aug. 30, 2018

(65) Prior Publication Data
US 2019/0365947 A1 Dec. 5, 2019

(30) Foreign Application Priority Data
Feb. 23, 2017 (JP) .............................. JP2017-032743

(51) Int. Cl.
| | | |
|---|---|---|
| *A61L 27/16* | (2006.01) | |
| *A61L 27/34* | (2006.01) | |
| *A61L 27/38* | (2006.01) | |
| *A61L 27/54* | (2006.01) | |
| *C12M 3/00* | (2006.01) | |
| *C12N 5/071* | (2010.01) | |

(52) U.S. Cl.
CPC ............... *A61L 27/16* (2013.01); *A61L 27/34* (2013.01); *A61L 27/3804* (2013.01); *A61L 27/54* (2013.01); *C12M 21/08* (2013.01); *C12N 5/0671* (2013.01); *C12N 5/0677* (2013.01); *A61L 2300/412* (2013.01); *A61L 2300/606* (2013.01); *A61L 2300/64* (2013.01); *A61L 2400/18* (2013.01); *A61L 2420/02* (2013.01); *A61L 2430/28* (2013.01); *A61L 2430/40* (2013.01)

(58) Field of Classification Search
CPC ........ A61K 35/22; A61K 35/26; A61K 35/28; A61K 35/35; A61K 35/50; A61K 35/55; A61K 9/00; A61K 9/06; A61L 2420/02; A61L 27/16
See application file for complete search history.

(56) References Cited

U.S. PATENT DOCUMENTS

| | | |
|---|---|---|
| 5,529,914 A | 6/1996 | Hubbell et al. |
| 2006/0246043 A1 | 11/2006 | Inoue et al. |
| 2008/0193536 A1 | 8/2008 | Khademhosseini et al. |
| 2015/0175961 A1 | 6/2015 | Chaudhry et al. |
| 2016/0271988 A1 | 9/2016 | Oharuda et al. |

FOREIGN PATENT DOCUMENTS

| | | | |
|---|---|---|---|
| EP | H10-287711 | * | 10/1998 |
| EP | 2030997 B1 | * | 1/2007 |
| JP | 10-043286 A | | 2/1998 |
| JP | 10-287711 A | | 10/1998 |
| JP | H10-287711 | | 10/1998 |
| JP | 2004-331643 A | | 11/2004 |
| JP | 2015-78324 A | | 4/2015 |
| RU | 2461625 C2 | | 12/2010 |

OTHER PUBLICATIONS

Sumi et al, title: Review: macro-encapsulation of islets in polyvinyl alcohol hydrogel , Journal of Medical and Biological engineering, 2014, vol. 34; No. 3; pp. 204-210 (Year: 2014).*
Krystyna Burczak, et al; title: Long-term in tivo performance and biocompatibility of poly(vinyl alcohol) hydrogel macrocapsules for hybridtype artificial pancreas; Biomaterials, vol. 17, issue 24, pp. 2351-2356, published 1996. (Year: 1996).*
Rainbow et al, titel: An Introduction to Materials in Medicine; Biomaterial Science, 3rd edition, Chapter II.6.15, 2013 (Year: 2013).*
Meloche, title: transplantation for the treatment of type 1 diabetes; World J Gastroenterol 2007; vol. 13, issue 47, pp. 6347-6355 (Year: 2007).*
Lee et al, title: human albumin preserves islet mass and function better than whole serum during pretransplantation islet culture; Transplantation Proceedings vol. 40, Issue 2, Mar. 2008, pp. 384-386) (Year: 2008).*
Burczak, Bomaterials, vol. 17, issue 24, pp. 2351-235 (Year: 1996).*
Meloche ,(World J Gastroenterol; vol. 13, issue 47, pp. 6347-6355). (Year: 2007).*
Burczak, Krystyna et al., "Long-term in vivo performance and biocompatibility of poly(vinyl alcohol) hydrogel macrocapsules for hybrid-type artificial pancreas" Biomaterials, 1996, pp. 2351-2356, vol. 17.
Sakata, Naoaki et al., "Effectiveness of bone marrow cell loading encapsulated pancreatic islet" The Uehara Memorial Foundation Research Report Collection, 2012, pp. 1-4, vol. 26, No. 163.
Sumi, Shoichiro et al., "Review: Macro-Encapsulation of Islets in Polyvinyl Alcohol Hydrogel" Journal of Medical and Biological Engineering, 2014, pp. 204-210, vol. 34, No. 3.
Yoshimatsu, G. et al., "Development of Polyvinyl Alcohol Bioartificial Pancreas with Rat Islets and Mesenchymal Stem Cells" Transplantation Proceedings, 2013, pp. 1875-1880, vol. 45.
International Search Report for PCT/JP2018/006661 dated May 5, 2018.
International Preliminary Report on Patentability for PCT/JP2018/006661 dated Aug. 29, 2019.
Supplementary European Search Report dated Dec. 2, 2020 issued for EP 18757458.7.
Wang et al., "Progress in islet cell transplantation" Xinjiang Medicine Journal, vol. 43, 2013.

* cited by examiner

*Primary Examiner* — Carlos A Azpuru
(74) *Attorney, Agent, or Firm* — Knobbe, Martens, Olson & Bear, LLP

(57) ABSTRACT

A cell or tissue embedding device having an aqueous gel serving as an immunoisolation layer, the aqueous gel containing, as components thereof, a denatured polyvinyl alcohol resin having an activated carbonyl group and a cross-linking agent is highly capable of supplying a physiologically active substance.

19 Claims, 4 Drawing Sheets

CELL OR TISSUE EMBEDDING DEVICE

CROSS REFERENCE TO RELATED APPLICATIONS

This application is a U.S. National Phase Application of PCT International Application Number PCT/JP2018/006661, filed on Feb. 23, 2018, designating the United States of America and published in the Japanese language, which is an International Application of and claims the benefit of priority to Japanese Patent Application No. 2017-032743, filed on Feb. 23, 2017. The disclosures of the above-referenced applications are hereby expressly incorporated by reference in their entireties.

TECHNICAL FIELD

The present invention relates to an aqueous gel for forming an immunoisolation layer of a cell or tissue embedding device which enables transplantation of a biological component that produces and/or secretes a physiologically active substance, such as a hormone or a protein, useful for a living organism, or of a biological component that has a detoxifying action on a harmful substance, and after the transplantation, exerts a preventive and/or therapeutic effect on diseases in animals including humans, such as an endocrine disease and a metabolic disease.

BACKGROUND ART

A cell or tissue embedding device is a device which contains living cells, living tissue, or the like and is used as a substitute for an organ etc. of a diseased human or animal for the purpose of preventing and/or treating a disease in a patient by supplying, to the patient, a hormone, a protein, or other physiologically active substances associated with metabolic function, or detoxifying a harmful substance. The cell or tissue embedding device is advantageous in that the living cells or living tissue can be protected by the immunoisolation layer from the biological defense mechanism and therefore the need for immunosuppressant administration and associated side effects can be avoided unlike living organ transplantation, that the operation is less invasive, and that the device enables, in addition to homologous artificial organ transplantation from a dead donor, transplantation of various regenerated stem cells and heterologous artificial organ transplantation, solving the problem of donor shortage.

In recent years, studies have been made on cell or tissue embedding devices comprising a material, such as a general polymer, a metal, or a ceramic, combined with living cells or living tissue or a cell preparation thereof, and such a device can be applied to the treatment of various diseases by changing the kind of the cells or the like contained therein.

For example, bioartificial pancreatic islets containing insulin-secreting cells (for example, pancreatic islet cells) are used to supply insulin as a hormone to a patient to thereby improve the blood sugar level.

In addition, bioartificial organs, such as a blood coagulation factor producing bio-artificial organ, a growth hormone producing bio-artificial organ, a parathyroid hormone producing bio-artificial organ, and a dopamine producing bio-artificial organ, are under examination for the therapy of diseases, such as hemophilia, hypophyseal dwarfism, hypoparathyroidism, and Parkinson's disease.

The cell or tissue embedding devices are supplied in various forms, and examples thereof include a device using a microcapsule or macrocapsule preparation in which living cells or living tissue is encapsulated in a polymer (for example, cell preparation). Such a device is characterized in that the strong cross-linked structure of the polymer protects the cells or tissue from the biological defense mechanism and that a hormone or the like secreted from the cells or tissue is supplied to a living organism using the molecular permeability of the polymer.

In recent years, polyvinyl alcohol (hereinafter may be abbreviated to PVA) has attracted attention as a polymer used for a bio-artificial organ etc. in which macrocapsule cell preparation is used.

PVA is a highly safe material which can be made into a gel by a chemical or physical treatment. PVA has a relatively high gel strength, and can be formed into various shapes. Examples of the chemical treatment used include a method in which glutaraldehyde (a crosslinking agent) and hydrochloric acid (a catalyst) are added to an aqueous solution containing PVA (see, for example, Non Patent Literature 1). Examples of the physical treatment used include a method in which an aqueous solution containing PVA is made into a gel by rapid cooling at a low temperature of about −20° C. (Patent Literature 1).

CITATION LIST

Patent Literature

Patent literature 1: JP 10-43286 A
Patent literature 2: JP 2004-331643 A

Non Patent Literature

Non Patent Literature 1: Krystyna Burczak et al., Long-term in vivo performance and biocompatibility of PVA hydrogelmacrocapsules for hybrid-type artificial pancreas, Biomaterials, 1996, vol. 17, 2351-2356

SUMMARY OF INVENTION

Technical Problem

The gelation method using a chemical treatment as described above has a problem of cell damage caused by the crosslinking agent remaining in the PVA gel or by the low pH level after the addition of the catalyst, which reduces the number of living cells or the capability of supplying the physiologically active substance. As a result, the desired treatment effect cannot be obtained.

The gelation method using a physical treatment does not use any chemical agent and does not cause damage by a crosslinking agent or a catalyst, but the rapid cooling at the low temperature reduces the number of living cells or the capability of supplying the physiologically active substance.

As a method for solving these problems, disclosed is a method in which the preparation of the PVA gel at a low temperature is performed in the co-existence of a cell preservative with living cells (Patent literature 2). However, in this method also, a low temperature (−80° C.) treatment for 24 hours is performed to prepare a PVA gel, and therefore, the problem of reducing the number of living cells or the capability of supplying the physiologically active substance cannot be sufficiently solved.

In light of the current situation described above, an object of the present invention is to provide a cell or tissue embedding device highly capable of supplying a physiologically active substance, by curbing the reduction of living cells or living tissue in the process of preparing a PVA gel containing the living cells or living tissue.

Solution to Problem

To achieve the above object, the present inventors conducted intensive investigations and found that when a polymer material having a main chain resistant to in vivo enzymatic cleavage and having an activated carbonyl group is used, a less toxic crosslinking agent may be used and gelation may be carried out under desired (i.e., less harmful to living cells or living tissue to be embedded) pH and temperature conditions, enabling gelation under optimum conditions for living cells or living tissue. In a verification experiment using a PVA gel as a most preferable embodiment, it was confirmed that a PVA-gel cell (or tissue) preparation having a high survival rate of cells or tissue in the PVA gel and a high capability of supplying a physiologically active substance was obtainable. The present inventors conducted further examination and completed the present invention.

That is, the present invention relates to the following (1) to (25).

(1) A cell or tissue embedding device having an aqueous gel serving as an immunoisolation layer, the aqueous gel containing, as components thereof, a denatured polyvinyl alcohol resin having an activated carbonyl group (A) and a crosslinking agent (B).
(2) The cell or tissue embedding device according to the above (1), wherein the aqueous gel has a history of gelation at a temperature of −5° C. or higher.
(3) The cell or tissue embedding device according to the above (1) or (2), wherein the aqueous gel has a stress of 0.5 to 100 kPa.
(4) The cell or tissue embedding device according to any one of the above (1) to (3), wherein the denatured polyvinyl alcohol resin having an activated carbonyl group (A) is diacetone acrylamide-denatured polyvinyl alcohol.
(5) The cell or tissue embedding device according to the above (4), wherein the diacetone acrylamide-denatured polyvinyl alcohol contains 0.5 to 15 mol % diacetone acrylamide unit relative to the whole denatured polyvinyl alcohol.
(6) The cell or tissue embedding device according to any one of the above (1) to (5), wherein the crosslinking agent (B) is a hydrazide compound and/or a semicarbazide compound.
(7) The cell or tissue embedding device according to any one of the above (1) to (5), wherein the crosslinking agent (B) is adipic acid dihydrazide or aminopolyacrylamide.
(8) The cell or tissue embedding device according to any one of the above (1) to (7), wherein a biological component (C) and a cell culture component (D) are embedded in the immunoisolation layer.
(9) The cell or tissue embedding device according to the above (8), wherein the biological component (C) is one or more selected from the group consisting of pancreatic islet cells, pancreatic ductal cells, liver cells, nerve cells, thyroid cells, parathyroid cells, kidney cells, adrenal cells, pituitary cells, splenic cells, fat cells, bone marrow cells, mesenchymal stem cells, ES cells, and iPS cells.
(10) The cell or tissue embedding device according to the above (8), wherein the biological component (C) is pancreatic islet cells or liver cells.
(11) The cell or tissue embedding device according to any one of the above (8) to (10), wherein the cell culture component (D) is an acetate or phosphate buffer containing one or more selected from the group consisting of Na, K, Cl, Ca, and glucose.
(12) The cell or tissue embedding device according to any one of the above (1) to (11), having a stress of 0.5 to 100 kPa.
(13) The cell or tissue embedding device according to any one of the above (1) to (12), comprising a supporting base (E).
(14) The cell or tissue embedding device according to the above (13), wherein the material of the supporting base (E) is one or more selected from the group consisting of PET, PE, PP, Teflon, and metal.
(15) A method for producing the cell or tissue embedding device according to any one of the above (8) to (14), comprising the steps of mixing an aqueous solution containing a denatured polyvinyl alcohol resin having an activated carbonyl group (A) with a crosslinking agent (B) and a cell culture component (D), subsequently mixing a biological component (C) therewith, and subjecting the obtained mixture to gelation.
(16) The method for producing the cell or tissue embedding device according to the above (15), wherein an aqueous gel is prepared at a temperature of −5° C. or higher.
(17) An immunoisolation layer forming agent for a cell or tissue embedding device, the agent containing an aqueous gel containing a denatured polyvinyl alcohol resin having an activated carbonyl group (A) and a crosslinking agent (B), wherein the crosslinking agent (B) is adipic acid dihydrazide or aminopolyacrylamide.
(18) The agent according to the above (17), wherein the denatured polyvinyl alcohol resin having an activated carbonyl group (A) is diacetone acrylamide-denatured polyvinyl alcohol.
(19) The agent according to the above (18), wherein the diacetone acrylamide-denatured polyvinyl alcohol contains 0.5 to 15 mol % diacetone acrylamide unit relative to the whole denatured polyvinyl alcohol.
(20) Use of the aqueous gel according to any one of the above (1) to (14) and (17) to (19), for producing the device according to any one of the above (1) to (13).
(21) A method for preventing or treating a disease in a human or an animal, characterized in that the device according to any one of the above (1) to (14) is administered to a human or an animal.
(22) The device according to any one of the above (1) to (14) for use in preventing or treating a disease in a human or an animal.
(23) A cell or living tissue embedding device having an aqueous gel serving as an immunoisolation layer, the aqueous gel containing a denatured polyvinyl alcohol resin having an activated carbonyl group (A) and allowing penetration of a component secreted by a biological component (C) embedded therein while inhibiting penetration of immune-related cells or an immune-related substance. (Here, the component secreted by the biological component (C) is preferably a physiologically active substance, such as a hormone or a protein useful for a living organism.)
(24) A mixture containing a denatured polyvinyl alcohol resin having an activated carbonyl group (A), a crosslinking agent (B), a biological component (C), and a cell culture component (D), the mixture having a property of forming a gel at a temperature of −5° C. or higher.
(25) A method for forming a protecting gel layer for cells or tissue producing a physiologically active substance, the method comprising applying an aqueous solution or a sol of a protecting gel layer-forming material containing a gel-forming polymer material and a crosslinking agent to the cells or tissue, optionally supported on a supporting material, at a temperature of 60° C. or lower, the gel-forming polymer material having a main chain resistant to in vivo enzymatic cleavage and having an activated carbonyl group, and subjecting the solution or sol to gelation at a temperature of −5° C. or higher.

Advantageous Effects of Invention

Since the cell or tissue embedding device of the present invention is produced using a gel-forming polymer material having a main chain resistant to in vivo enzymatic cleavage, a long device life can be achieved when applied into a living organism. In addition, since the cell or tissue embedding device of the present invention is produced using less toxic components and an aqueous gel can be formed at a pH and a temperature (preferably −5° C. or higher) less harmful to the living cells or living tissue to be embedded or less likely to kill the living cells or living tissue to be embedded, the device is highly capable of supplying a physiologically active substance, such as a hormone or a protein, useful for a patient.

That is, the cell or tissue embedding device of the present invention achieves a high survival rate of the cells or tissue embedded therein.

In addition, by administering the cell or tissue embedding device of the present invention to a patient, prevention and/or treatment of a disease, such as an endocrine disease, a metabolic disease, diabetes, a neurodegenerative disease, hemophilia, a bone disease, and cancer, can be performed and the cells or tissue can be stably held in a living organism for a long period of time. Therefore, a high cure rate can be achieved and the frequency of the cell or tissue embedding device transplantation can be reduced.

Furthermore, the aqueous gel such as the aqueous PVA gel as a representative embodiment of the present invention (herein, may be referred to as the aqueous gel of the present invention) can inhibit penetration of complements in addition to leucocytes, antibodies, etc., and therefore, can isolate the environment from not only cells and antibodies participating in immunity but also complements that assist immunological effects. That is, the aqueous PVA gel of the present invention allows penetration of molecules having a diameter of about 5 nm, which presumably corresponds to the diameter of the maximum one among various molecules that should be passed therethrough, including oxygen, inorganic and organic nutrients, and various hormones (for example, physiologically active substances including hormones, such as insulin) while the aqueous PVA gel does not allow penetration of molecules having a diameter of about 50 nm, which presumably corresponds to the diameter of the minimum one among immune-related cells and immune-related substances (for example, antibodies and complements) that should not be passed therethrough. Due to the selectivity, the aqueous PVA gel can be used as an immunoisolation layer, having an excellent immunosuppressive effect.

DESCRIPTION OF EMBODIMENTS

Figure 1:
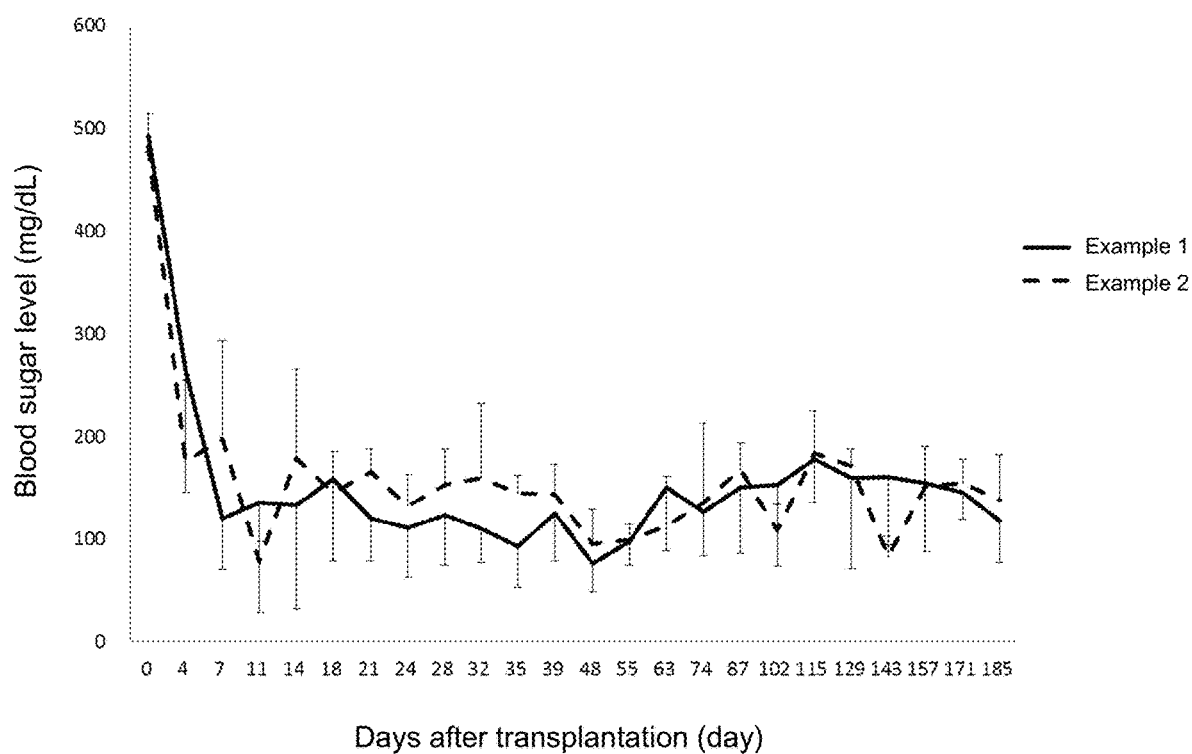
FIG. 1 shows the temporal change of the blood sugar levels of diabetic model animals after transplantation of the bioartificial pancreatic islet devices of Example 1 and Example 2.

Hereinafter, the present invention will be described in detail.

The disclosure encompasses a cell or tissue embedding device having an aqueous gel serving as an immunoisolation layer, the aqueous gel that can be prepared in the form of an aqueous solution or a sol containing, as components thereof, a gel-forming polymer material having a main chain resistant to in vivo enzymatic cleavage and an activated carbonyl group, for example, a denatured polyvinyl alcohol resin having an activated carbonyl group (A), and a crosslinking agent (B), the gel-forming polymer material being capable of forming a gel at a temperature of −5° C. or higher. For more significant exertion of the effects of the present invention, the gel-forming polymer material having a main chain resistant to in vivo enzymatic cleavage and an activated carbonyl group, exemplified by a denatured polyvinyl alcohol resin (A), preferably reacts with a crosslinking agent (B) to form a crosslinked 3-dimensional net structure in the aqueous gel or the cell or tissue embedding device.

A representative embodiment of the aqueous gel of the present invention is an aqueous gel for forming an immunoisolation layer of a cell or tissue embedding device, the aqueous gel containing, as components thereof, a gel-forming polymer material having a main chain resistant to in vivo enzymatic cleavage and a carbonyl group, for example, a denatured polyvinyl alcohol resin having an activated carbonyl group (A), and a crosslinking agent (B). The aqueous gel is prepared by subjecting an aqueous solution or a sol containing the components to temperature reduction to not lower than −5° C.

In this disclosure, the sol is preferably a hydrosol.

A Gel-Forming Polymer Material Having a Main Chain Resistant to In Vivo Enzymatic Cleavage and Having an Activated Carbonyl Group The gel-forming polymer material used in the present invention having a main chain resistant to in vivo enzymatic cleavage and having an activated carbonyl group, unlike gelatin or alginic acid as an aqueous gel-forming material used for the same purpose, is preferably a polymer material having a main chain resistant to in vivo enzymatic cleavage, and, for example, may additionally have a main chain to be broken at either or both ends as long as the principal part is not broken. Such a material is exemplified by a polymer having an ethylene structure as a main chain of its repeating unit, in particular, a polyvinyl alcohol resin and a polyacrylic acid resin, and among them, preferred is a polymer material having, in addition to a functional group improving the hydrophilicity, an activated carbonyl group in its side chain. When such a material is used, even if the device is left in a living organism for a long time, the main chain is resistant to in vivo enzymatic cleavage, and therefore, the form of the device can be retained for a long time.

The activated carbonyl group is preferably a carbonyl group which easily reacts with a crosslinking agent, such as a hydrazide and a carbazide, having a nucleophilic functional group with a high nucleophilic reactivity, to bring about dehydration condensation or nucleophilic substitution, leading to crosslinking between the resins. As a result, gelation can be performed at a pH and a temperature less harmful to embedded living cells or living tissue. Specific examples of the activated carbonyl group include ones having an aldehyde structure or a ketone structure, and also ones having an ester structure with a highly desorptive alcoholic component can also be used.

Hereinafter, detailed description will be given based on a case where a denatured polyvinyl alcohol resin is used as a representative embodiment of the present invention.

Denatured PVA Resin (A)

As the denatured polyvinyl alcohol resin having an activated carbonyl group (A) (herein may be simply referred to as "denatured PVA resin (A)"), for example, a denatured-by-copolymerization PVA, which is produced by copolymerization of an aliphatic vinyl ester with an unsaturated monomer having an activated carbonyl group and by subsequent saponification of the resulting copolymer, or a post-denatured PVA, which is obtained by direct contact of a PVA or a denatured PVA resin produced by a known method with a compound having an activated carbonyl group, such as liquefied diketene or diketene gas, may be used. However, for better stability and safety of the PVA resin and for better workability in the gelation step, denatured-by-copolymerization PVA is preferred.

The aliphatic vinyl ester used in the production of the denatured-by-copolymerization PVA is not particularly limited, and examples thereof include vinyl formate, vinyl acetate, vinyl propionate, and vinyl pivalate. Among them, vinyl acetate is industrially preferred. These can be produced by a publicly known polymerization method, such as bulk polymerization, solution polymerization, suspension polymerization, emulsion polymerization, etc. Among these, solution polymerization with the use of an alcoholic solvent, such as methanol, is industrially preferred.

The unsaturated monomer having an activated carbonyl group is not particularly limited, but diacetone acrylamide is industrially preferable. As the denatured-by-copolymerization PVA, a PVA denatured with diacetone acrylamide is preferred.

In the present invention, in the copolymerization of the aliphatic vinyl ester and the unsaturated monomer having an activated carbonyl group, other unsaturated monomers capable of copolymerizing with an aliphatic vinyl ester and an unsaturated monomer having an activated carbonyl group may be used as long as the effects of the present invention are not impaired.

Examples of such other unsaturated monomers may be one or more kinds selected from carboxyl group-containing unsaturated monomers, such as (meth)acrylic acid, maleic acid, maleic anhydride, fumaric acid, crotonic acid, itaconic acid, and undecylenic acid; unsaturated dibasic-acid monoalkyl esters, such as monomethyl maleate and monomethyl itaconate; amide group-containing unsaturated monomers, such as acrylamide, dimethylacrylamide, dimethylaminoethylacrylamide, diethylacrylamide, dimethylaminopropylacrylamide, isopropylacrylamide, N-methylolacrylamide, and N-vinylacetamide; vinyl halides, such as vinyl chloride and vinyl fluoride; glycidyl group-containing unsaturated monomers, such as allyl glycidyl ether and glycidyl methacrylate; lactam group-containing unsaturated monomers, such as N-vinyl-pyrrolidones, such as N-vinyl-2-pyrrolidone, and N-vinyl-alkyl-pyrrolidone, such as N-vinyl-mono- or di-$C_{1-4}$ alkyl-pyrrolidone, such as N-vinyl-3-propyl-2-pyrrolidone, N-vinyl-5-methyl-2-pyrrolidone, N-vinyl-5-ethyl-2-pyrrolidone, N-vinyl-5,5-dimethyl-2-pyrrolidone, and N-vinyl-3,5-dimethyl-2-pyrrolidone; N-allyl-pyrrolidones, such as N-allyl-2-pyrrolidone; N-vinyl-piperidones, such as N-vinyl-2-piperidone and N-vinyl-alkyl-piperidone, such as N-vinyl-mono- or di-$C_{1-4}$ alkyl-piperidones, such as N-vinyl-6-methyl-2-piperidone and N-vinyl-6-ethyl-2-piperidone; N-vinyl-caprolactams, such as N-vinyl-epsilon-caprolactam and N-vinyl-alkyl-caprolactam, such as N-vinyl-mono- or di-$C_{1-4}$ alkyl-caprolactams, such as N-vinyl-7-methyl-2-caprolactam and N-vinyl-7-ethyl-2-caprolactam; alkyl vinyl ethers, such as $C_{1-20}$ alkyl vinyl ethers, such as methyl vinyl ether, n-propyl vinyl ether, i-propyl vinyl ether, n-butyl vinyl ether, i-butyl vinyl ether, t-butyl vinyl ether, lauryl vinyl ether, dodecyl vinyl ether, and stearyl vinyl ether; nitriles, such as acrylonitrile and methacrylonitrile; hydroxyl group-containing unsaturated monomers, such as $C_{1-20}$ monoalkyl allyl alcohols, such as allyl alcohol and isopropenyl allyl alcohol, $C_{1-20}$ dialkyl allyl alcohols, such as dimethyl allyl alcohol, and hydroxy $C_{1-20}$ alkyl vinyl ethers, such as hydroxy ethyl vinyl ether and hydroxybutyl vinyl ether; acetyl group-containing unsaturated monomers, such as $C_{1-20}$ alkyl allyl acetates, such as allyl acetate, dimethylallyl acetate, and isopropenylallyl acetate; (meth)acrylic acid esters, such as (meth)acrylic acid alkyl esters, such as (meth)acrylic acid $C_{1-20}$ alkyl esters, such as methyl (meth)acrylate, ethyl (meth)acrylate, 2-ethylhexyl acrylate, and n-butyl acrylate; vinylsilanes, such as trimethoxyvinylsilane, tributylvinylsilane, and diphenylmethylvinyl silane; polyoxyalkylene (meth) acrylates, such as polyoxyethylene (meth)acrylate and polyoxypropylene (meth) acrylate; polyoxyalkylene (meth)acrylamides, such as polyoxyethylene (meth) acrylamide and polyoxypropylene (meth) acrylamide; polyoxyalkylene vinyl ethers, such as polyoxyethylene vinyl ether and polyoxypropylene vinyl ether; polyoxyalkylene alkylvinyl ethers, such as polyoxyethylene allyl ether, polyoxypropylene allyl ether, polyoxyethylene butylvinyl ether, and polyoxypropylene butylvinyl ether; α-olefins, such as ethylene, propylene, n-butene, and 1-hexene; butenes, such as 3,4-dihydroxy-1-butene, 3,4-diacyloxy-1-butene, 3-acyloxy-4-hydroxy-1-butene, 4-acyloxy-3-hydroxy-1-butene, and 3,4-diacyloxy-2-methyl-1-butene; pentenes, such as 4,5-dihydroxy-1-pentene, 4,5-diacyloxy-1-pentene, 4,5-dihydroxy-3-methyl-1-pentene, and 4,5-diacyloxy-3-methyl-1-pentene; hexenes, such as 5,6-dihydroxy-1-hexene and 5,6-diacyloxy-1-hexene; amine unsaturated monomers, such as N,N-dimethylallylamine, N-allylpiperazine, 3-piperidine acrylic acid ethyl ester, 2-vinylpyridine, 4-vinylpyridine, 2-methyl-6-vinylpyridine, 5-ethyl vinylpyridine, 5-butenylpyridine, 4-pentenylpyridine, and 2-(4-pyridyl)allyl alcohol; quaternary ammonium compound-containing unsaturated monomers, such as dimethylaminoethyl acrylate methyl chloride quaternary salt, N,N-dimethylaminopropylacrylamide methyl chloride quaternary salt, and N,N-dimethylaminopropylacrylamide methyl benzenesulfonate quaternary salt; aromatic unsaturated monomers, such as styrene; sulfonic acid group-containing unsaturated monomers, such as 2-acrylamide-2-methylpropanesulfonic acid or its alkali metal salt, ammonium salt or organic amine salt, 2-acrylamide-1-methylpropanesulfonic acid or its alkali metal salt, ammonium salt or organic amine salt, 2-methacrylamide-2-methylpropanesulfonic acid or its alkali metal salt, ammonium salt or organic amine salt, vinyl sulfonic acid or its alkali metal salt, ammonium salt or organic amine salt, allyl sulfonic acid or its alkali metal salt, ammonium salt or organic amine salt, and methallyl sulfonic acid or its alkali metal salt, ammonium salt or organic amine salt; glycerol monoallyl ether; 2,3-diacetoxy-1-allyloxypropane; 2-acetoxy-1-allyloxy-3-hydroxypropane; 3-acetoxy-1-allyloxy-3-hydroxypropane; 3-acetoxy-1-allyloxy-2-hydroxypropane; glycerol monovinyl ether; glycerol monoisopropenyl ether; acryloyl morpholine; vinyl ethylene carbonate; vinylimidazole; and vinylcarbazole.

The amount of such other unsaturated monomers is not particularly limited, and for example, may be 10 mol or less relative to 100 mol of the vinyl ester monomer.

In addition, as long as the effects of the present invention are not impaired, the obtained denatured-by-copolymerization PVA may be post-denatured by a known method using a reaction, such as acetalization, urethanation, etherification, grafting, phosphorylation, acetoacetylation, cationization, etc.

The polymerization catalyst used in the production of the denatured-by-copolymerization PVA is not particularly limited, and an azo compound or a peroxide is usually used.

During the polymerization, an organic acid, such as tartaric acid, citric acid, and acetic acid, may be added for the purpose of preventing the hydrolysis of the aliphatic vinyl ester.

To terminate the polymerization, a polymerization terminator may be optionally used. The polymerization terminator is not particularly limited, and examples thereof include m-dinitrobenzene etc.

In the copolymerization of the aliphatic vinyl ester and the unsaturated monomer having an activated carbonyl group in the present invention, the shape of the polymerization vessel, the type of the polymerization agitator, the polymerization temperature, the pressure in the polymerization vessel, etc. may be the same as those in a publicly known method.

In the present invention, the saponification method of the copolymer of the aliphatic vinyl ester and the unsaturated monomer having an activated carbonyl group is not particularly limited, and a conventionally known method may be used. For example, a conventionally known alcoholysis or hydrolysis using a basic catalyst, such as sodium hydroxide, potassium hydroxide, and sodium methoxide, or an acidic catalyst, such as hydrochloric acid, sulfuric acid, and p-toluenesulfonic acid, is applicable.

Examples of the solvent used for the saponification include alcohols, such as methanol and ethanol; esters, such as methyl acetate; ketones, such as acetone and methyl ethyl ketone; aromatic hydrocarbons, such as benzene and toluene; tetrahydrofuran, etc., and these may be used alone or in combination of two or more kinds. The saponification temperature, saponification time, etc. are not particularly limited.

Also, the method for drying, grinding, or washing the saponification product is not particularly limited, and a publicly known method may be used.

When a PVA denatured with diacetone acrylamide is used as the denatured PVA, the diacetone acrylamide unit content is, for example, 0.5 to 20 mol %, preferably 0.5 to 15 mol %, more preferably 1 to 12 mol %, and still more preferably 2 to 10 mol % (for example, 3 to 8 mol %). When the diacetone acrylamide unit content is 0.5 mol % or more, many reaction sites with the crosslinking agent exist and a sufficient strength (stress) for a cell or tissue embedding device can be obtained, and when the diacetone acrylamide unit content is 20 mol % or less, an improved solubility in water can be obtained. In view of these points, the above range is preferred.

The saponification degree of the denatured PVA resin (A) is not particularly limited, but preferably 80 mol % or higher (for example, 80 to 99.9 mol %), more preferably 88 mol % or higher (for example, 88 to 99.9 mol %), and still more preferably 95 mol % or higher (for example, 95 to 99.9 mol %).

The viscosity of the denatured PVA resin (A) may be varied, and the 4 mass % aqueous solution viscosity of the denatured PVA resin (A) is preferably 2 to 500 mPa·s, more preferably 3 to 300 mPa·s, and still more preferably 5 to 200 mPa·s (for example, 5 to 80 mPa·s). The saponification degree and the viscosity of a 4 mass % aqueous solution were measured in accordance with JIS K-6726.

Crosslinking Agent (B)

The crosslinking agent (B) is preferably one having a functional group reactive with a carbonyl group (for example, amino group etc.).

Examples of the crosslinking agent (B) include a hydrazide compound, a semicarbazide compound, and the like. In particular, preferred are a hydrazide compound, a semicarbazide compound, and the like having 2 or more functional groups in the molecule, the functional group being selected from the group consisting of the following formulae (1) to (3). The crosslinking agent used may be of one kind or two or more kinds in combination.

—NH—NH$_2$  (1)

—CO—NH—NH$_2$  (2)

—NH—CO—NH—NH$_2$  (3)

Specific examples of the hydrazide compound include carbohydrazide, dicarboxylic hydrazide (aliphatic dicarboxylic hydrazide, such as oxalic dihydrazide, malonic dihydrazide, succinic dihydrazide, glutaric dihydrazide, adipic dihydrazide, pimelic dihydrazide, suberic dihydrazide, azelaic dihydrazide, sebacic dihydrazide, dodecane dihydrazide, and hexadecane dihydrazide; aromatic dicarboxylic hydrazide, such as terephthalic dihydrazide, isophthalic dihydrazide, 2,6-naphthoic dihydrazide, and 4,4'-bisbenzene dihydrazide; alicycle dicarboxylic hydrazide, such as 1,4-cyclohexanedicarboxylic dihydrazide; hydroxyl-containing dicarboxylic dihydrazide, such as tartaric dihydrazide and malic dihydrazide; iminodiacetic dihydrazide; itaconic dihydrazide; etc.), 1,3-bis(hydrazinocarbonoethyl)-5-isopropylhydantoin, 7,11-octadecadiene-1,18-dicarbohydrazide, tris (2-hydrazinocarbonyl-ethyl)isocyanurate, citric trihydrazide, butane tricarbohydrazide, 1,2,3-benzene trihydrazide, ethylenediaminetetraacetic tetrahydrazide, 1,4,5,8-naphthoic tetrahydrazide, nitriloacetic trihydrazide, cyclohexanetricarboxylic trihydrazide, pyromellitic tetrahydrazide, etc.

Examples of the semicarbazide compound include N,N'-hexamethylene bissemicarbazide, and biuretry-tri(hexamethylene semicarbazide).

Also, derivatives obtained by reactions between these hydrazide compounds or semicarbazide compounds and low boiling point ketones, such as acetone and methylethylketone, may be used.

Among the above crosslinking agents (B), preferred are dicarboxylic hydrazide, aminopolyacrylamide, etc., more preferred are adipic dihydrazide, aminopolyacrylamide, etc., and particularly preferred is aminopolyacrylamide in view of low toxicity, high solubility in water, etc.

As the crosslinking agent (B), one kind or a combination of two or more kinds of the above crosslinking agents may be used.

The amount of the crosslinking agent (B) to be added is preferably 1 to 30 parts by mass, more preferably 2 to 25 parts by mass, and still more preferably 3 to 20 parts by mass (for example, 4 to 15 parts by mass) relative to 100 parts by mass of the denatured PVA resin (A). When the amount is 1 part by mass or more, a high crosslinking density and a sufficient strength (stress) for a cell or tissue embedding device can be obtained, and when the amount is 30 parts by mass or less, the residual amount of unreacted crosslinking agent can be reduced. In view of these points, the above range is preferred.

When aminopolyacrylamide is used as the cross linking agent (B), the molecular weight range is not particularly limited, and may be adjusted such that the effects of the present invention are not impaired. The weight-average molecular weight (Mw) is preferably about 3000 to 6000000, more preferably about 5000 to 1000000, and further more preferably about 8000 to 800000 (for example, about 10000 to 300000, about 10000 to 200000, about 10000 to 100000, etc.).

When aminopolyacrylamide is used as the crosslinking agent (B), the hydrazidation rate of the aminopolyacrylamide is not particularly limited, and may be adjusted such that the effects of the present invention are not impaired. The hydrazidation rate is preferably 30% or higher, more preferably 40% or higher, and further more preferably 50% or higher (for example, 60% or higher).

The molecular weight and the hydrazidation rate of the aminopolyacrylamide may be appropriately adjusted within the range where the effects of the present invention are not impaired. The adjustment may be made by, for example, increasing the hydrazidation rate for a lower molecular weight, or reducing the hydrazidation rate for a higher molecular weight.

The crosslinking rate, the void ratio, and/or the average pore diameter of the aqueous PVA gel of the present invention may be adjusted such that the selectivity of the aqueous PVA gel is not impaired. The selectivity of the aqueous PVA gel means that the aqueous PVA gel allows penetration of molecules having a diameter of about 5 nm, which presumably corresponds to the diameter of the maximum one among various molecules that should be passed therethrough, including oxygen, inorganic and organic nutrients, and various hormones (for example, physiologically active substances including hormones, such as insulin) while the aqueous PVA gel does not allow penetration of molecules having a diameter of about 50 nm, which presumably corresponds to the diameter of the minimum one among immune-related cells and immune-related substances (for example, antibodies and complements) that should not be passed therethrough. Examples of a method useful for such adjustment include the complement penetration blocking test described later.

The average pore size of the aqueous PVA gel of the present invention is, for example, 5 nm or more and less than 500 nm, preferably 5 nm or more and less than 200 nm, and more preferably 5 nm or more and less than 50 nm.

The average pore size can be determined by a publicly known method. The average pore size can be determined by, for example, by photographing (SEM image, 1000× to 5000× magnification) the gel surface using a scanning electron microscope (Hitachi S-4000 made by Hitachi, Ltd.), importing the obtained image into an image processor (main body: TV image processor TVIP-4100II made by Nippon Avionics Co., Ltd; control software: TV image processor image command 4198 made by Ratoc System Engineering Co., Ltd.) to measure the sizes of a predetermined number of pores, and then arithmetically processing the sizes.

Alternatively, the average pore size can be determined using an atmospheric force scanning electron microscope (for example, AeroSurf (registered trade mark) 1500, made by Hitachi High-Technologies; and JASM-6200 made by JEOL, Ltd.), or by dynamic light scattering (for example, nano Partica SZ-100-Plus made by Horiba, Ltd.), scanning microscopic light scattering, etc.

The aqueous PVA gel usually has such a strength (stress) as to prevent easy collapse at the time of transplantation. The stress varies depending on the 4% aqueous solution viscosity, the modification degree, the type and the added amount of the crosslinking agent, and the solid concentration of the aqueous PVA gel, and therefore cannot be simply determined, but for example, the stress is 0.5 to 100 kPa, preferably 0.6 to 95 kPa, more preferably 0.7 to 90 kPa, and still more preferably 0.7 to 85 kPa.

The stress of the aqueous PVA gel can be measured using a compact table-top tester EZ Test EZ-SX made by Shimadzu Corporation, according to the directions for use.

Biological Component (C)

By embedding a biological component (C) in the aqueous gel of the present invention, a cell or tissue embedding device can be formed.

The biological component (C) is not particularly limited, and can be appropriately selected according to the intended use of the cell or tissue embedding device to be produced.

The biological component (C) is preferably cells (preferably living cells) or living tissue that can be stably stored at a temperature preferable for the production of the aqueous gel of the present invention (i.e., −5 to 60° C.) because, in this case, a cell or tissue embedding device highly capable of supplying a physiologically active substance can be obtained regardless of the kind of the cells or living tissue.

As such cells, differentiated cells, stem cells, or the like derived from ectoderm, mesoderm, or entoderm can be used, for example.

As the differentiated cells, for example, epidermal cells, smooth muscle cells, bone cells, bone marrow cells, cartilage cells, skeletal myoblasts, pancreatic parenchymal cells, pancreatic islet cells, pancreatic endocrine cells, pancreatic exocrine cells, pancreatic ductal cells, liver cells (for example, hepatocytes), thyroid cells, parathyroid cells, adrenal cells, pituitary cells, splenic cells, pineal cells, renal cells (nephrocytes), spleen cells, anterior pituitary cells, somatotropic cells, dopamine-producing cells, blood cells, cardiac muscle cells, skeletal muscle cells, osteoblast cells, nerve cells, pigment cells, fat cells, etc. can be used. The above cells are not limited to cells isolated from a living organism and may be cells differentiated from stem cells described later.

As for stem cells (iPS cells etc.) and other cells that can be induced to differentiate, the cells may be embedded in the device, and after administration, differentiated in a living organism. Alternatively, the cells may be differentiated beforehand and then embedded in the device.

The stem cells may be tissue stem cells (for example, epidermal stem cells, hair follicle stem cells, pancreatic stem cells/pancreatic progenitor cells, liver stem cells, neural stem cells, retinal stem cells, hematopoietic stem cells, mesenchymal stem cells, etc.), embryonic stem cells (ES cells), iPS cells (induced pluripotent stem cells), etc., but are not limited thereto.

These cells are preferably from a mammal, such as a human, a swine, a rat, or a mouse, and preferably produce and/or secrete a physiologically active substance, such as a hormone or a protein, useful for a living organism, such as a patient. The kind of the cells to be selected may be determined depending on the kind of the disease in the living organism, such as a patient, to undergo the transplantation. In the cases where these cells are not human cells, they may be cells having a human gene introduced thereinto for therapeutic purposes. The hormone useful for a living organism may be exemplified by insulin, thyrotropic hormone, thyroid hormone, parathyroid hormone, growth hormone, thyroxine, glucocorticoid, glucagon, estradiol, and testosterone. The protein useful for a living organism may be exemplified by, in particular, a blood coagulation factor, a complement, albumin, globulin, and various enzymes (metabolic enzymes or digestive enzymes, such as amylase, protease, and lipase). Examples of other physiologically active substances include neurotransmitters, such as dopamine.

Specifically, the cells are preferably pancreatic cells (pancreatic islet cells), hepatocytes, dopamine-producing cells, and stem cells and progenitor cells thereof, more preferably pancreatic cells (pancreatic islet cells), hepatocytes, and stem cells and progenitor cells thereof, and more preferably pancreatic cells (pancreatic islet cells) and pancreatic progenitor (stem) cells.

The biological component (C) used in the present invention may be cells or living tissue established for laboratory use, cells separated from living tissue, or the like, and preferably differentiated non-dividing cells. The separation method is not particularly limited, and the separation may be performed according to a conventionally known method. Desirably, cells separated from living tissue are subjected to removal of pathogens, such as pathogenic viruses.

In the cell or tissue embedding device of the present invention, the amount of the biological component (C) may be appropriately changed according to the kind of the biological component (C) and is not particularly limited. The content is, for example, 1000 to 1000000 cells, preferably 10000 to 100000 cells, and more preferably 20000 to 50000 cells per cubic millimeter of the gel device embedding space.

The dosage amount cannot be definitely specified because it is determined on a case-by-case basis by a doctor in consideration of the patient's age, sex, and conditions, side effects, etc., but usually, the number of devices to be transplanted in the body per adult is about 1 to 10. For example, into a diabetic patient, usually 1000 to 100000 IEQ (international unit of the number of pancreatic islets: 1 IEQ corresponds to the volume of one islet with a diameter of 150 μm), preferably 5000 to 40000 IEQ, more preferably 10000 to 20000 IEQ per kg of the patient's body weight contained in one or more devices may be transplanted.

The shape of the device is not particularly limited. The shape may be discoidal, globular, cylindrical, ellipsoidal, or the like, and a discoidal shape is preferred. When the device is discoidal, the size may be represented as the product of the thickness and the diameter. The thickness is usually 0.1 mm to 10 cm, preferably 0.1 to 5 mm, and more preferably 0.5 to 2 mm, and the diameter is usually about 1 mm to 50 cm, preferably about 1 mm to 10 cm, and more preferably about 2 to 4 cm.

A conventionally known material may be used in the device.

As the biological component (C) in the present invention, in addition to the above-described cells or living tissue, other components of biological origin may be included.

The disclosure encompasses cases other than the cases where cells or tissue in the cell or tissue embedding device of the present invention is from living microorganisms.

Cell Culture Component (D)

In the aqueous gel of the present invention, a cell culture component (D) may be embedded together with the biological component (C) to form a cell or tissue embedding device.

The cell culture component (D) is not particularly limited, and examples thereof include an acetate or phosphate buffer containing Na, K, Cl, Ca, and glucose.

When Na is contained in the cell culture component (D), the Na concentration is preferably adjusted to 20 to 150 mEq/L, and more preferably adjusted to 80 to 140 mEq/L.

When K is contained, the K concentration is preferably adjusted to 2.5 to 130 mEq/L, and more preferably adjusted to 3.5 to 40 mEq/L.

When Cl is contained, the Cl concentration is preferably adjusted to 15 to 170 mEq/L, and more preferably adjusted to 100 to 150 mEq/L.

When Ca is contained, the Ca concentration is preferably adjusted to 0.5 to 5 mEq/L, and more preferably adjusted to 1 to 3 mEq/L.

When glucose is contained, the glucose concentration is preferably adjusted to 1 to 11 mM, and more preferably adjusted to 3 to 7 mM.

The cell culture component (D) is not particularly limited, and examples thereof include a publicly known cell culture medium, such as HBSS (Hanks' balanced salt solution), a commercial preservation solution, such as Euro-Collins solution, CELLBANKER, and UW solution (University of Wisconsin solution), a cellular protection component, such as dimethyl sulfoxide (DMSO) and serum albumin, a component for preventing contamination by germs, such as an antibiotic, a component for retaining cell activity, such as vitamins, such as nicotinamide, etc., and a publicly known cell culture medium or the like is preferred. These may be used alone or in combination of two or more kinds thereof.

The cell culture component (D) may be used in combination with another component (for example, a sustained-releasability imparting agent, a tonicity agent, a pH adjuster, etc.).

Since the denatured PVA resin (A) and the cell culture component (D) are in contact with each other in the device of the present invention, when the cell culture component (D) is added in the preparation of the device, it is convenient to add the cell culture component (D) at a concentration as high as "(the volume of the solution containing polyvinyl alcohol resin (A)+the volume of crosslinking agent (B)+the volume of cell culture component (D))/the volume of cell culture component (D)" times the final concentration.

The amount of the cell culture component (D) in this state is not particularly limited, but the content is preferably such that the growth, survival, and/or physiologically active substance secretion of the cells or the living tissue is not inhibited and the object of the present invention is not impaired.

The amount of the cell culture component (D) added in the state described above may be, for example, about 100 to 2000 parts by mass, preferably about 150 to 1000 parts by mass (for example, 200 to 300 parts by mass, 175 to 300 parts by mass, etc.) relative to 100 parts by mass of the denatured PVA resin (A).

For example, the cell culture component (D) at a concentration as high as 10 times the final concentration may be 1 mL relative to 8 mL of the denatured PVA resin (A) solution and 1 mL of the crosslinking agent (B).

In the preparation of the cell or tissue embedding device, components other than the denatured PVA resin (A), the crosslinking agent (B), the biological component (C), and the cell culture component (D) may be used.

Examples of such other components include a cell growth factor, which is a substance that promotes or controls the growth of living cells, a cytokine, which is an active substance produced from a cell, another physiologically active substance, a blood-flow promoter, which promotes the blood flow to the cell or tissue embedding device, a neurotrophic factor, etc. These may be used alone or in combination of two or more kinds thereof.

Examples of the cell growth factor include a platelet derived growth factor (PDGF), an epidermal growth factor (EGF), a fibroblast growth factor (FGF), a hepatocyte growth factor (HGF), a vascular endothelial growth factor (VEGF), insulin, etc.

Examples of the cytokine include a hematopoietic factor (for example, interleukins, chemokines, a colony-stimulating factor, etc.), a tumor necrosis factor, interferons, etc.

Examples of the physiologically active substance other than the cell growth factor and the cytokine include amino acids (for example, glycine, phenylalanine, lysine, aspartic acid, glutamic acid, etc.), vitamins (for example, biotin, pantothenic acid, vitamin D, etc.), serum albumin, an antibiotic, etc.

Examples of the blood-flow promoter include citrulline or its salt, capsaicin, and capsaicinoids.

Examples of the neurotrophic factor include NGF (nerve growth factor), BDNF (brain-derived neurotrophic factor; brain-derived neurotrophic factor), NT-3 (neurotrophin-3), NT-4 (neurotrophin-4), GDNF (glial-cell derived neurotrophic factor), neurturin, artemin, persephin, etc.

The amounts of the above components are not particularly limited.

Aqueous Gel

The aqueous gel used in the cell or tissue embedding device of the present invention can be prepared, for example, as follows: an aqueous solution of a denatured PVA resin (A) is prepared, and then mixed with a crosslinking agent (B) or an aqueous solution of a crosslinking agent (B) prepared beforehand. The obtained mixture may be centrifuged.

The biological component (C) may be mixed with the aqueous gel after the preparation of the aqueous gel. Or alternatively, when the crosslinking agent (B) or its aqueous solution is added to and mixed with the aqueous solution of the denatured PVA resin (A), the biological component (C) may also be added and mixed therewith.

In the addition of the crosslinking agent (B) or the aqueous solution of the crosslinking agent (B) and the biological component (C) to the aqueous solution of the denatured PVA resin (A), the order of addition is not particularly limited, and it is possible that the biological component (C) is added to a mixture obtained by the addition of the crosslinking agent (B) or its aqueous solution to the aqueous solution of the denatured PVA resin (A), that the crosslinking agent (B) or its aqueous solution is added to a mixture obtained by the addition of the biological component (C) to the aqueous solution of the denatured PVA resin (A), and that the crosslinking agent (B) or its aqueous solution and the biological component (C) are simultaneously added to the aqueous solution of the denatured PVA resin (A).

Regarding the cell culture component (D), it is possible that the aqueous gel prepared beforehand is immersed in a solution containing the cell culture component (D), and that the cell culture component (D) is mixed with the denatured PVA resin (A) and the crosslinking agent (B) (and also the biological component (C) as needed) in the preparation of the aqueous gel, but for curbing the reduction of the number of living cells, the cell culture component (D) may be mixed with the denatured PVA resin (A) and the crosslinking agent (B) (and also the biological component (C) as needed) before the gelation.

In a more preferred method for preparing the aqueous gel, an aqueous solution of the denatured PVA resin (A), the crosslinking agent (B) (or its aqueous solution), and the cell culture component (D) are mixed, the biological component (C) is added thereto, and the resulting mixture (may be in a sol state) is subjected to gelation.

The above-mentioned other components that may be used in the present invention may be added together with or separately from the biological component (C) and/or the cell culture component (D), to the denatured PVA resin (A), an aqueous solution of the denatured PVA resin (A), the crosslinking agent (B), and/or the aqueous gel, and then be mixed therewith.

The method for preparing the aqueous solution of the denatured PVA resin (A) is not particularly limited, and the preparation can be achieved by, for example, a conventionally known method for dissolving PVA, in which the resin (A) is dispersed in water at room temperature, the temperature is raised to 80° C. or higher with stirring, and after complete dissolution, the solution is cooled.

The method for preparing the aqueous solution of the crosslinking agent (B) is not particularly limited, and the preparation can be achieved by, for example, a method in which the crosslinking agent (B) is dispersed in water at room temperature and the dispersion is stirred at room temperature until dissolution, or a method in which the dispersion is stirred under heating (for example, at 60° C. for 10 minutes) and then left stand at room temperature.

The aqueous solution of the denatured PVA resin (A) or the aqueous solution of the crosslinking agent (B) is desirably sterilized by a conventionally known method, such as autoclave treatment, UV or gamma-ray treatment, or the like, and in the mixing with the biological component (C) or subsequent production of the cell or tissue embedding device, the operation and storage are desirably performed under a germ-free environment.

The pH of the mixture of the crosslinking agent (B) and the denatured PVA resin (A) (and also the biological component (C) and/or the cell culture component (D) is mixed therewith as needed) is preferably adjusted to 6.0 to 8.0, more preferably 6.2 to 7.7, and still more preferably 6.5 to 7.5 using a buffer, such as HEPES (2-[4-(2-hydroxyethyl)-1-piperazinyl]ethanesulfonic acid). This range is preferable because living cells or living tissue to be embedded in the cell or tissue embedding device is less likely to be damaged and the reduction of the number of living cells is curbed.

In the preparation of the aqueous gel, the mixture of an aqueous solution of the denatured PVA resin (A) and the crosslinking agent (B) (and also the biological component (C) and/or the cell culture component (D) is mixed therewith as needed) (or an aqueous solution of the mixture) may be left stand.

The temperature at which the mixture is left stand is not particularly limited as long as the temperature is suitable for storing living cells, and is, for example, −5° C. or higher, preferably −5 to 60° C. (for example, 0 to 60° C.), more preferably −3 to 50° C. (for example, 0 to 50° C.), and still more preferably 0 to 40° C. In this range, the reduction of the number of living cells is curbed, which is preferable. The temperature at which the mixture is left stand is preferably such that the aqueous solution (may be in a sol state) or an aqueous gel of the denatured PVA resin (A) and the crosslinking agent (B) does not freeze and living cells or living tissue can be embedded in the solution or the aqueous gel. In the present invention, by using the denatured PVA resin (A), it is possible to prepare an aqueous gel at a relatively low temperature suitable for storing living cells or living tissue (for example, a temperature within the above range).

The left-stand time for the preparation of the aqueous gel may be appropriately selected depending on the concentration of the denatured PVA resin (A), the amount of the crosslinking agent (B), the left-stand temperature, or the like, and is usually about 1 hour to 3 or 4 days. One hour or more of the left-stand time is preferred from the viewpoints including that the resulting cell or tissue embedding device does not easily collapse when placed in a living organism.

By adding a pH buffer or the like to the mixture of the denatured PVA resin (A) and the crosslinking agent (B) (and also the biological component (C) and/or the cell culture component (D) is mixed therewith as needed), the time required for gelation can be controlled. Lower pH of the system tends to reduce the gelation time and higher pH tends to increase the gelation time.

When the proportion of the number of living cells in the aqueous gel or in the cell or tissue embedding device relative to the total number of the living cells in the biological component (C) immediately before embedded in the aqueous gel is higher as compared to that in the aqueous gel or in the cell or tissue embedding device not containing, as components thereof, the denatured PVA resin (A) and the crosslinking agent (B), the cell or tissue embedding device of the present invention can be regarded as achieving a high survival rate of the cells or tissue embedded therein.

The proportion of the number of living cells in the aqueous gel or in the cell or tissue embedding device relative to the total number of the living cells in the biological component (C) immediately before embedded in the aqueous gel is, for example, 60 to 100%, preferably 70 to 100%, and more preferably 80 to 100%. The number of living cells can be determined by, for example, cytoplasmic staining with fluorescein diacetate, and nuclear staining with propidium iodide (sometimes abbreviated to FDA/PI measurement).

The solid concentration in the aqueous gel is, for example, 0.3 to 20%, preferably 0.5 to 10%, and more preferably 1 to 8% (for example, 3 to 8%). When the solid concentration is in the range, after the cell or tissue embedding device is transplanted into an animal, the form and the immunoisolation capability of the device can be retained in the body for a long period of time. In view of such points, the above range is preferable. Herein, the method for measuring the solid concentration is not particularly limited, and may be, for example, a method using a heating-and-drying moisture analyzer (A&D, MS-70) or the like as in Examples described later.

The resulting aqueous gel has a structure suitable for functioning as an immunoisolation layer described later, i.e., a structure that stably maintains cells, allows oxygen, glucose, hormones useful for a living organism such as insulin, and other physiologically active substances to pass therethrough and does not allow immune-related proteins to pass therethrough.

The shape of the aqueous gel is not particularly limited, and examples thereof include sheets, boards, discs, rods, tubes, beads, etc.

Examples of the method for forming the shape of the aqueous gel include a method in which an aqueous solution (may be in a sol state) containing the denatured PVA resin (A) and the crosslinking agent (B) (and also preferably the biological component (C) and the cell culture component (D) as desired) is poured into a mold having an intended shape before gelation, a method in which an obtained gel is shaped into an intended shape with a knife or the like, etc.

Usually, the aqueous solution containing the denatured PVA resin (A) and the crosslinking agent (B) (and also the biological component (C) and/or the cell culture component (D), etc. as desired) goes through a sol state before reaching the gel state. Such a sol state shall be regarded as an equivalent to the aqueous gel of the present invention and is understood to be also included in the present invention.

The solid concentration in the aqueous solution (may be in a sol state) containing the denatured PVA resin (A) and the crosslinking agent (B) is, for example 0.3 to 20%, preferably 0.5 to 10%, and more preferably 1 to 8%. When the solid concentration is in the range, after the cell or tissue embedding device is transplanted into an animal, the form and the immunoisolation capability of the device can be retained in the body for a long period of time. In view of such points, the above range is preferable.

Cell or Tissue Embedding Device

The aqueous gel of the present invention can be used as an immunoisolation layer of a cell or tissue embedding device.

The "immunoisolation layer" means a layer that allows penetration of, for example, glucose; hormones, such as insulin, thyrotropic hormone, thyroid hormone, parathyroid hormone, growth hormone, thyroxine, glucocorticoid, glucagon, estradiol, and testosterone; proteins, such as a blood coagulation factor, albumin, globulin, and various enzymes (metabolic enzymes or digestive enzymes, such as amylase, protease, and lipase); neurotransmitters, such as dopamine; etc., but does not allow penetration of, for example, immune-related proteins, such as antibodies, complements, and leucocytes.

The cell or tissue embedding device embeds or contains the biological component (C), and may be, for example, a bio-artificial organ.

The method for producing the cell or tissue embedding device is not particularly limited, and for example, by storing (for example, for about 1 hour to 3 or 4 days) an aqueous solution or an aqueous gel containing the PVA resin (A) containing the biological component (C) and the cell culture component (D) in a mold having an intended shape at a temperature of 0 to 40° C. (for example, 4° C.), a cell or tissue embedding device can be produced.

The tissue embedding device usually has such a strength (stress) as to prevent easy collapse at the time of transplantation. The stress varies depending on the 4% aqueous solution viscosity, the modification degree, the type and the added amount of the crosslinking agent, and the solid concentration of the tissue embedding device, and therefore cannot be simply determined, but for example, the stress is 0.5 to 100 kPa, preferably 0.6 to 95 kPa, more preferably 0.7 to 90 kPa, and still more preferably 0.7 to 85 kPa.

The stress of the tissue embedding device can be measured using a compact table-top tester EZ Test EZ-SX made by Shimadzu Corporation, according to the directions for use.

The cell or tissue embedding device of the present invention may comprise a supporting base (E).

The aqueous gel may be used in combination with a supporting base (E) useful as a reinforcing material for the reinforcement and/or easier handling.

For example, in cases where the aqueous gel is formed into a thin film, gelation is preferably performed on a base (reinforcing material) such as a resin mesh sheet for the reinforcement and easier handling.

The material of the supporting base (E) is not particularly limited, and examples thereof include polymers (for example, PET (polyethylene terephthalate), PE (polyethylene), PP (polypropylene), Teflon (registered trade mark), etc.), metals, and the like. The material is preferably not altered or decomposed in a living organism, but may be decomposed after a certain period of time.

The mesh size of the mesh sheet is determined such that the mesh allows penetration of molecules having a diameter of about 5 nm, which presumably corresponds to the diameter of the maximum one among various molecules that should be passed therethrough, including oxygen, inorganic and organic nutrients, and various hormones (for example, physiologically active substances including hormones, such as insulin) while the mesh does not allow penetration of molecules having a diameter of about 50 nm, which presumably corresponds to the diameter of the minimum one among immune-related cells and immune-related substances (for example, antibodies and complements) that should not be passed therethrough. For this reason, the mesh size is usually 5 to 100 nm, preferably 10 to 50 nm, and more preferably 20 to 30 nm.

A preferred embodiment of the cell or tissue embedding device of the present invention has, for example, a configuration obtained as follows. On a glass slide, an aqueous solution or an aqueous gel containing a denatured PVA resin (A) and a crosslinking agent (B), containing the cell culture component (D) is placed; on this, a supporting base (E), such as a PET mesh (for example, trade name: PET mesh sheet TN120 etc. made by SANPLATEC Corp.) is placed; on the PET mesh sheet, a suspension obtained by suspending a biological component (C) in an aqueous solution or an aqueous gel containing a denatured PVA resin (A) and a crosslinking agent (B) is placed; the suspension is spread over the PET mesh using a gel loading tip etc.; a PET mesh is further placed thereon in such a manner that the suspension is between the PET meshes; further on the PET mesh, an aqueous solution or an aqueous gel containing a denatured PVA resin (A) and a crosslinking agent (B), containing the cell culture component (D) is placed; on this, a glass slide is placed; and the glass slides are removed. Before the glass slides are removed, the cell or tissue embedding device is preferably left stand at a temperature of 0 to 40° C. (for example, 4° C.) for 2 to 72 hours, and more preferably for 3 to 48 hours.

The cell or tissue embedding device of the present invention can be transplanted by being placed in a body, such as under the skin, under the fascia, on the liver surface, on the spleen surface, in the greater omentum, or in the abdominal cavity of an animal including a human. The method for placing the device is not particularly limited, and a conventionally known method may be employed. For example, an instrument used for the transplantation may be a publicly known one.

By transplanting the cell or tissue embedding device of the present invention into an animal including a human having an endocrine disease (for example, a thyroid disease, a parathyroid disease, an adrenal disease, a pituitary disease, a pineal disease, etc.), a metabolic disease (for example, ornithine transcarbamylase deficiency, hyperammonemia, hypercholesterolemia, homocystinuria, glycogenosis, Crigler Najjar syndrome, Wilson's disease, etc.), diabetes (for example, Type 1 diabetes, Type 2 diabetes, pancreatic diabetes, etc.), a neurodegenerative disease (for example, Parkinson's disease, Alzheimer disease, amyotrophic lateral sclerosis, spinocerebellar degeneration, etc.), hemophilia, a bone disease (for example, osteoporosis etc.), cancer (for example, leukemia etc.), etc., the prevention and/or therapy of the diseases can be achieved. Since the cell or tissue embedding device of the present invention can retain the cells in a stable state in a living organism, these diseases can be treated at a high cure rate, and the frequency of the cell or tissue embedding device transplantation can be reduced.

Furthermore, the aqueous gel of the present invention can inhibit penetration of, in addition to particles having a particle diameter of 5 to 50 μm (for example, leucocytes (for example, macrophages etc.), lymphocyte (for example, T lymphocyte etc.), etc.), particles having a particle diameter of 0.1 to 1 μm (for example, complements etc.). Therefore, the cell or tissue embedding device of the present invention can isolate the environment from immune-related cells and complements, and for this reason, can be used as an excellent immunoisolation layer.

As a preferable embodiment, a case where the cells are pancreatic islet cells, for example, will be described.

Figure 4:
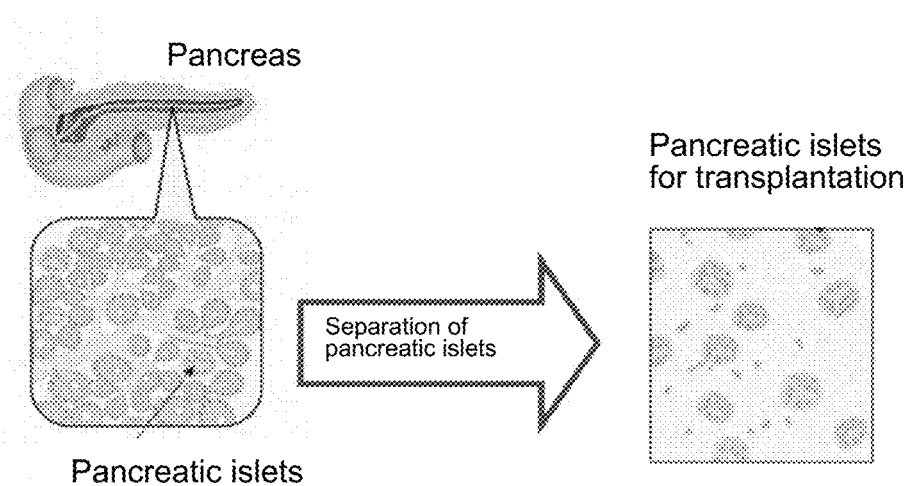
FIG. 4 schematically shows an embodiment of a method for obtaining pancreatic islet cells from the pancreas.
Figure 5:
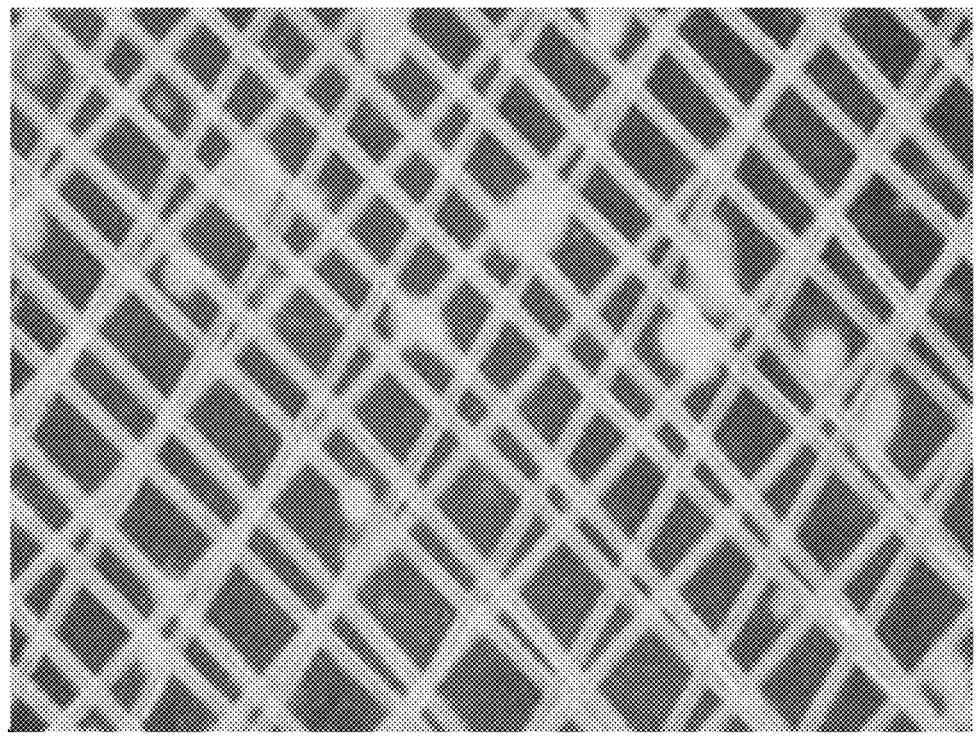
FIG. 5 shows an example of a state where pancreatic islet cells are immobilized between two meshes, the cells being prevented from aggregating.
Figure 6:
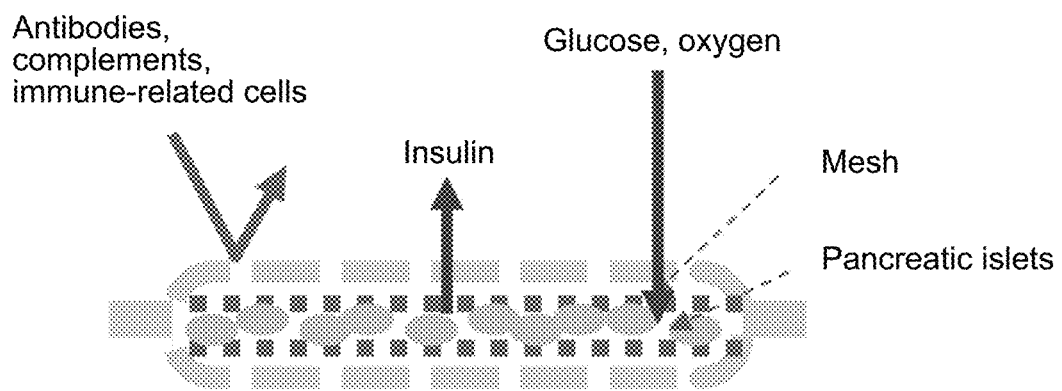
FIG. 6 shows one embodiment of a cell or tissue embedding device having an aqueous gel serving as an immunoisolation layer, the aqueous gel containing, as components thereof, a denatured polyvinyl alcohol resin having an activated carbonyl group (A) and a crosslinking agent (B).

As shown in FIG. 4, pancreatic islet cells of good quality are separated from the pancreas to prepare pancreatic islets for transplantation (see FIG. 4). In order to prevent aggregation of the pancreatic islet cells, the cells are fixed between the above-described meshes (two sheets) (see FIG. 5). From the thus-prepared pancreatic islet cells in the fixed state, the denatured PVA resin having an activated carbonyl group (A), and the crosslinking agent, the device of the present invention is produced, where the most inner layer is pancreatic islet cells secreting insulin. The second layer is a mesh layer supporting the cells. The outermost layer is a gel surface forming an immunoisolation membrane. The immunoisolation membrane has a high biocompatibility, and allows insulin to pass therethrough but does not allow immune-related substances to pass therethrough (see FIG. 6).

Figure 7:
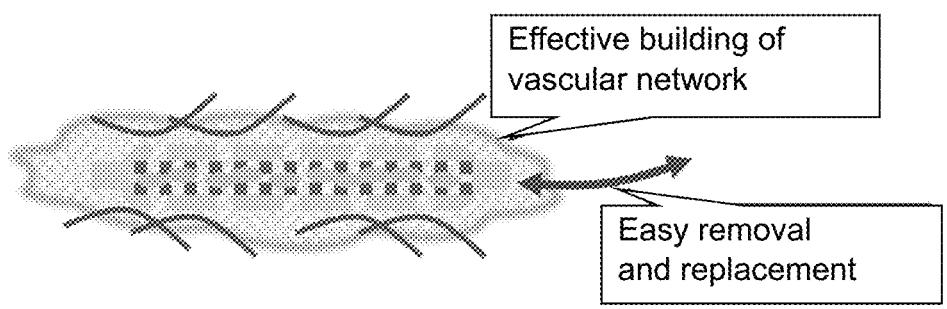
FIG. 7 schematically shows an example of a state where the device of the present invention is administered into and accommodated in a network of neovascular vessels.

The device of the present invention can be applied as it is into a living organism living organism, and is, for example, accommodated in a network built of neovascular vessels, which can be easily provided according to the known art, to exhibit a medical effect. The device can be easily taken out or replaced (see FIG. 7).

This device can provide at least one of the following features.
(1) Maintains high quality of the cells embedded.
(2) Appropriately isolates the transplanted pancreatic islets from the host patient's immune system.
(3) Receives supply of oxygen and glucose and provides appropriate insulin response.
(4) Enables less invasive transplantation and can be easily taken out of the body or replaced as needed.

The cell or tissue embedding device of the present invention preferably does not have a semipermeable membrane.

EXAMPLES

Hereinafter, the present invention will be illustrated in more detail by Examples, but the present invention is not limited thereto. Various modifications can be made within the technical idea of the present invention by those with ordinary skill in the art. In Examples, "parts" and "%" express "parts by mass" and "% by mass" unless otherwise stated.

Preparation of Denatured PVA Resin

Synthetic Example 1

Into a flask equipped with a stirrer, a thermometer, a dropping funnel, and a reflux condenser, 2000 parts of vinyl acetate, 143 parts of methanol, and 3.7 parts of diacetone acrylamide were placed. After nitrogen replacement of the system, the internal temperature was raised to 60° C. To the system, a solution of 0.16 part of 2,2-azobisisobutyronitrile dissolved in 100 parts of methanol was added to start polymerization. While nitrogen was continuously passed through the flask, a solution of 70.1 parts of diacetone acrylamide dissolved in 46.7 parts of methanol was continuously added dropwise at a constant rate from the start of polymerization. At 210 minutes from the start, m-dinitrobenzene as a polymerization terminator was added to stop the polymerization. The yield at the end of polymerization was 47.1%. The obtained reaction mixture was subjected to distillation of remaining vinyl acetate with continuous addition of methanol vapor, and thus a 35% methanol solution of a diacetone acrylamide-vinyl acetate copolymer was obtained. To 500 parts of this solution, 70 parts of methanol, 1 part of ion-exchange water, and 29.3 parts of a 4% methanol solution of sodium hydroxide were added and thoroughly mixed, and saponification was allowed to proceed at 45° C. The obtained gelatinous material was pulverized, thoroughly washed with methanol, and dried to give a PVA denatured with diacetone acrylamide. The viscosity of a 4% aqueous solution was 53.4 mPa·s, the saponification degree was 98.4 mol %, and the diacetone unit content was 3.6 mol %.

In this Synthetic Example 1, physical properties were determined as follows.
(1) Viscosity of a 4% aqueous solution: determined according to JIS K-6726 (1994).
(2) Saponification degree: determined according to JIS K 6726 (1994).
(3) Diacetone acrylamide unit content: using DMSO-d6 as a solvent, $^1$H-NMR measurement was performed, and the content was calculated from the integral value of the assigned peak.

Synthetic Examples 4 to 11

The PVAs denatured with diacetone acrylamide shown in Table 1 were obtained in a similar manner to that in Synthetic Example 1 except that polymerization conditions, such as the amounts of vinyl acetate, diacetone acrylamide, methanol, and the initiator used and saponification conditions were changed. For the synthesis of the PVAs denatured with diacetone acrylamide, conventionally known synthesis methods (for example, the synthesis method described in JP 2015-78324 A etc.) may be used.

TABLE 1

|  | 4% aqueous solution viscosity mPa·s | Modification degree mol % | Saponification degree mol % |
| --- | --- | --- | --- |
| Synthetic Example 1 | 53.4 | 3.4 | 98.4 |
| Synthetic Example 4 | 6.6 | 3.4 | 98.8 |
| Synthetic Example 5 | 6.0 | 8.6 | 98.4 |
| Synthetic Example 6 | 11.2 | 4.3 | 99.0 |
| Synthetic Example 7 | 21.9 | 3.7 | 98.7 |
| Synthetic Example 8 | 23.7 | 6.3 | 98.6 |
| Synthetic Example 9 | 65.1 | 5.7 | 98.8 |
| Synthetic Example 10 | 154.5 | 5.3 | 98.6 |
| Synthetic Example 11 | 20.0 | 5.9 | 96.7 |

Preparation of Aminopolyacrylamide

Synthetic Example 2

To an aqueous solution obtained by mixing 20 g of polyacrylamide having a weight average molecular weight of about 40000 and 40 g of ion-exchange water, 16 g of hydrazine monohydrate was added, and a reaction was allowed to proceed at 80° C. for 15 hours. To the obtained mixture, ethanol was added, and the resulting precipitate was subjected to filtration, washing, and drying to give aminopolyacrylamide 1. The weight average molecular weight was about 53000, and the hydrazidation rate was 88%.

Synthetic Example 3

The reaction was allowed to proceed in the same manner as in Synthetic Example 2 except that polyacrylamide having a weight average molecular weight of about 15000 was used to give amino polyacrylamide 2. The weight average molecular weight was about 22000, and the hydrazidation rate was 80%.

Synthetic Example 12

The reaction was allowed to proceed in the same manner as in Synthetic Example 2 except that polyacrylamide having a weight average molecular weight of about 65000 was used to give amino polyacrylamide 2. The weight average molecular weight was about 88000, and the hydrazidation rate was 90%.

In Synthetic Examples 2, 3, and 12, physical properties were determined as follows.
(1) Weight average molecular weight: determined by size exclusion chromatography.
Conditions:
Solvent: 50 mM aqueous solution of sodium dihydrogen phosphate Polymer concentration: 1 mg/mL
Flow rate: 1.0 mL/min
Column temperature: 40° C.
Column: Shodex OHPack SB-803HQ, Shodex OHPack SB-805HQ
Standard: pullulan
Detector: RI
(2) Hydrazidation rate: determined by back titration of 12 using a sodium thiosulfate standard solution. The details of the experimental operation were as follows:
Experimental Operation:
1. An I$_2$/MeOH solution was prepared.
2. The I$_2$/MeOH solution was titrated with a 0.1 M sodium thiosulfate standard solution.
(The result of this measurement was 0.047 M.)
3. Each polymer sample was precisely weighed and dissolved in 20 mL of ion-exchange water.

4. A 0.047 M I$_2$/MeOH solution was added to 2.0 mL of the solution of 3.

5. Back titration of I$_2$ was performed using a 0.1 M sodium thiosulfate standard solution.

Example 1

Preparation of Aqueous Solution of Denatured PVA Resin (A) and Crosslinking Agent (B) in a Sol State In a 25-mL tube, 8.0 mL of a 6.25% aqueous solution of the PVA denatured with diacetone acrylamide prepared in Synthetic Example 1 was placed. To this, 1.0 mL of HBSS (Hanks' balanced salt solution) at 10-fold concentration was added, and the tube was shaken up and down for agitation. Then, spinning down was performed using a centrifuge (trade name: Hybrid high-speed refrigerated centrifuge 6200 made by Kubota Corporation), and the tube was left stand at 37° C. for 10 minutes. To this, 1 mL of a 5% aqueous solution of the aminopolyacrylamide 1 (hereinafter may be abbreviated to APA1) prepared as a crosslinking agent in Synthetic Example 2 was added, and the tube was shaken up and down 15 times. Spinning down was performed using a centrifuge, and the tube was shaken up and down 15 times again. After that, the tube was centrifuged at 3000 rpm at 25° C. for 1 minute, and left stand at 37° C. The viscosity of the obtained aqueous solution in a sol state was checked from time to time, and when the time for the sol to be dropletized reached 3 to 4 seconds and the sol was judged to be in the optimal state for pancreatic islet embedding, the tube was taken out of the hot bath, and left stand on ice for 1 minute. After that, the tube was centrifuged at 3000 rpm at 25° C. for 1 minute to give a sol having 5 w/v % of denatured PVA resin (A) and 0.5 w/v % of crosslinking agent (B). The obtained sol was transferred to a 3.5-cm dish.

Solid Concentration Measurement of Sol

The solid concentration of the sol was measured using a heating-and-drying moisture analyzer (A&D, MS-70). On the sample dish of the moisture analyzer, a glass fiber sheet was placed, and about 1 g of the sol was allowed to uniformly permeate into the sheet. Then, the solid content of the sol was measured under the conditions of the sample dish temperature of 120° C. and the measuring time (warming time) of 15 minutes. In the measurement, the moisture analyzer was set in a mode for displaying the solid content (%). The formula for calculating the solid content is mass after drying/mass before drying×100(%). The calculated solid concentration of the sol was 6.5%.

Preparation of Pancreatic Islet Cells

For separation of pancreatic islets, 11 to 14-week-old male Lewis rats (Japan SLC, Inc.) were used. A cold Hanks' balanced salt solution (HBSS) containing 0.8 mg/mL of collagenase type V (made by Sigma-Aldrich) dissolved therein was injected, through the rat common bile duct, to the pancreas of the rat, and the pancreas was digested at 37° C. for 12 minutes to separate pancreatic islets from the pancreatic tissue. Concentration gradient centrifuge was performed using Histopaque-1119 (made by Sigma-Aldrich) and Lymphoprep (AXIS-SHIELD, Norway), and pancreatic islets were collected. The pancreatic islets were cultured in an RPMI 1640 culture medium containing 5.5 mmol/L of glucose and 10% fetal bovine serum (FBS) under 5% CO2 at 37° C. overnight, and were used in the examination of Examples and the Comparative Examples.

Preparation of Pancreatic Islet Embedding Device

On a glass slide, 160 µL of the above-prepared sol on the dish was placed. A PET mesh (trade name: PET mesh sheet TN120 made by SANPLATEC Corp.) was placed thereon, and a suspension obtained by suspending the above-prepared pancreatic islet cells from which the culture medium components had been removed as thoroughly as possible in 50 µL of the sol was placed on the PET mesh. The suspension of the pancreatic islet cells was spread over the PET mesh using a gel loading tip, and a PET mesh was further placed thereon in such a manner that the suspension of the pancreatic islet cells was between the PET meshes. Further on the PET mesh, 140 µL of the sol was placed, and on this, a glass slide was placed. The thus-built sol was placed in a moist chamber, and left stand at 4° C. for 48 hours to give a pancreatic islet embedding device (aqueous gel).

Step of Storing Pancreatic Islet Embedding Device

The pancreatic islet embedding device built as above was taken off the glass slides, soaked in 5 mL/well of a preservation medium (RPMI1640 culture medium containing glucose adjusted to a concentration of 5.5 mM and 10% FBS) in a 6-well plate, and stored at 4° C. for about 16 hours.

Step of Transplantation

Transplantation was performed by placing the pancreatic islet embedding device (aqueous gel) after the above storage under the skin of a C57BL/6J mouse with streptozotocin-induced diabetes.

Evaluation of Healing of Diabetes

After the above transplantation, time-depending changes in the blood sugar level were measured to examine the healing effect (n=7). The mean±SD is shown in FIG. 1 and Table 1. A blood sugar level of 200 mg/dL or lower was judged as Good (diabetes was healed) and a blood sugar level of higher than 200 mg/dL was judged as Poor (a state of diabetes).

Example 2

Evaluation of healing of diabetes was performed (n=4) in the same manner as in Example 1 except that the aminopolyacrylamide 2 prepared in Synthetic Example 3 was used instead of the aminopolyacrylamide 1 prepared in Synthetic Example 2. The mean±SD is shown in FIG. 1 and Table 2.

As shown in FIG. 1, the diabetic model animals into each of which the pancreatic islet embedding device of the present invention was transplanted showed reduction in the blood sugar level from immediately after the transplantation, and even at 185 days after the transplantation, the improvement in the blood sugar level was still observed.

Also, harvesting the pancreatic islet embedding device at 180 days after the transplantation under the skin was attempted. In each case of Example 1 (n=7) and Example 2 (n=4), the device favorably retained its form without any collapse, demonstrating that the cell or tissue embedding device of the present invention was strong enough not to be decomposed in the body.

In the case of 3 w/v % of denatured PVA resin (A) and 0.3 w/v % of crosslinking agent (B), as compared to the case where the crosslinking agent (B) of Synthetic Example 12 was used, reduction in the blood sugar level was observed from immediately after the transplantation, and even at 185 days after the transplantation, the improvement in the blood sugar level was still observed.

Comparative Example 1

Composition of PVA Solution

For the preparation of a pancreatic islet device to be frozen and thawed, a PVA solution containing 3% PVA (having a polymerization degree of 5000 and a saponification degree of 99.3 mol %), 10% FBS (fetal bovine serum), 5% dimethyl sulfoxide, and 10 mM nicotinamide obtained by dissolving the solutes in an ETK (ET-Kyoto) solution was used.

Step of Embedding Pancreatic Islet Cells

In a 1.5-mL tube, Lewis rat pancreatic islet cells from which the culture medium components had been removed as thoroughly as possible were placed. To this, 1.0 mL of a cell banker (Juji Field Inc.) at 4° C. was added, and the pancreatic islet cells were suspended. After the cells were left stand on ice for 1 minute, the cell banker was removed. On a glass slide with a 1-mm spacer, a PET mesh (trade name: PET mesh sheet TN120, 10×15 mm, made by SANPLATEC Corp.) having the above PVA solution applied thereon was placed. Over the PET mesh, a suspension obtained by suspending only pancreatic islet cells in 160 µL of the PVA solution was spread, and on this, a PET mesh having the PVA solution applied thereon was placed. On this, a glass slide was placed, and thus a 1-mm thick pancreatic islet device to be frozen and thawed was prepared.

Step of Freezing, Thawing, and Storage

The prepared pancreatic islet device to be frozen and thawed was left stand at −80° C. for 24 hours, taken off the glass slides, and thawed in an ice-cooled UW solution (University of Wisconsin solution, organ preservation solution). Further, the device was soaked in the ice-cooled UW solution three times (for 5 minutes each) to replace the solution in the gel by the UW solution, and then stored in the UW solution at 4° C. for 24 hours.

Step of Culture

The UW solution on the surface of the device was washed off with 10 mL of an ice-cooled culture medium for pancreatic islet culture (RPMI1640 culture medium containing 5.5 mM glucose, 10% FBS, and an antibiotic). After that, the device was soaked in the culture medium (ice-cooled) three times (for 5 minutes each) to replace the solution in the gel by the culture medium, and then cultured in 3 mL of the culture medium at 37° C. for 24 hours.

Step of Transplantation

Transplantation was performed by placing the frozen and thawed pancreatic islet device after the above storage in the abdominal cavity of a C57BL/6J mouse with streptozotocin-induced diabetes, regarding which mouse graft survival was known to be more successful in the abdominal cavity than under the skin.

Evaluation of Healing of Diabetes

After the transplantation, in the same manner as in Example 1, the blood sugar level was measured over time, and the healing effect was evaluated. The results are shown in Table 2 and FIG. 2.

Comparative Examples 2 to 18

As shown in Table 2, except that the number of pancreatic islets and the number of devices to be transplanted were changed, frozen and thawed pancreatic islet devices were prepared and transplanted, and healing of diabetes was evaluated in the same manner as in Comparative Example 1. The results are shown in Table 2 and FIGS. 2 and 3.

In Table 2, the blood sugar levels at 185 days after transplantation are shown for Examples 1 and 2, and the blood sugar levels at 28 days after transplantation are shown for Comparative Examples 1 to 18.

TABLE 2

| | Blood sugar level at 185 days or 28 days after transplantation (mg/dL) | Evaluation of healing of diabetes |
|---|---|---|
| Example 1 | 117 | Good |
| Example 2 | 138 | Good |
| Comparative Example 1 | 501 | Poor |
| Comparative Example 2 | 501 | Poor |
| Comparative Example 3 | 461 | Poor |
| Comparative Example 4 | 432 | Poor |
| Comparative Example 5 | 501 | Poor |
| Comparative Example 6 | 475 | Poor |
| Comparative Example 7 | 436 | Poor |
| Comparative Example 8 | 481 | Poor |
| Comparative Example 9 | No data (Died 1 day after transplantation) | Poor |
| Comparative Example 10 | 492 | Poor |
| Comparative Example 11 | 448 | Poor |
| Comparative Example 12 | No data (Died 1 day after transplantation) | Poor |
| Comparative Example 13 | No data (Died 2 days after transplantation) | Poor |
| Comparative Example 14 | No data (Died 1 day after transplantation) | Poor |
| Comparative Example 15 | No data (Died 1 day after transplantation) | Poor |
| Comparative Example 16 | No data (Died 1 day after transplantation) | Poor |
| Comparative Example 17 | No data (Died 1 day after transplantation) | Poor |
| Comparative Example 18 | No data (Died 1 day after transplantation) | Poor |

TABLE 3

| Comparative Example | Number of pancreatic islets (IEQ) | Number of transplanted devices |
|---|---|---|
| 1 | 1,300 | 1 |
| 2 | | |
| 3 | | |
| 4 | 1,500 | 1 |
| 5 | | |
| 6 | 3,000 | 1 |
| 7 | | |
| 8 | 6,000 | 1 |
| 9 | | |
| 10 | | |
| 11 | | |
| 12 | | |
| 13 | 6,000 | 2 |
| 14 | 6,000 | 2 |
| 15 | 6,000 | 1 |
| 16 | | |
| 17 | 12,000 | 2 |
| 18 | | |

Figure 2:
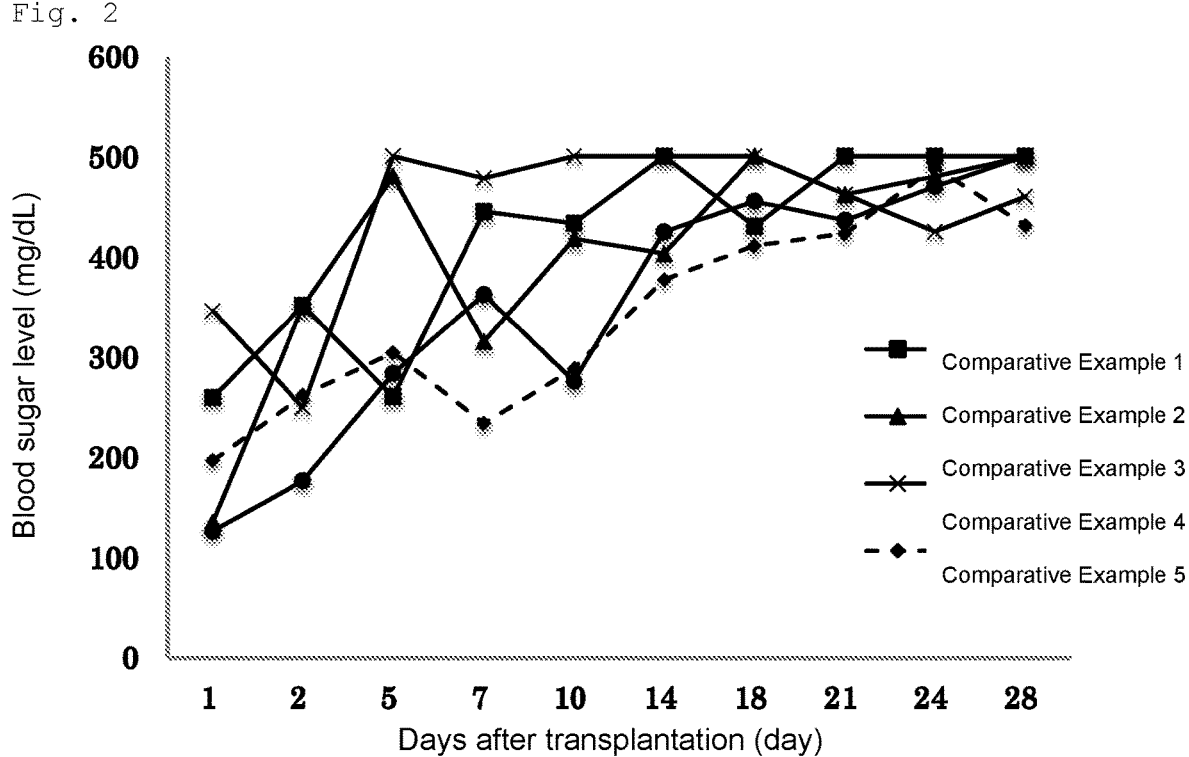
FIG. 2 shows the temporal change of the blood sugar levels of diabetic model animals after transplantation of the frozen and thawed pancreatic islet devices of Comparative Examples 1 to 5.
Figure 3:
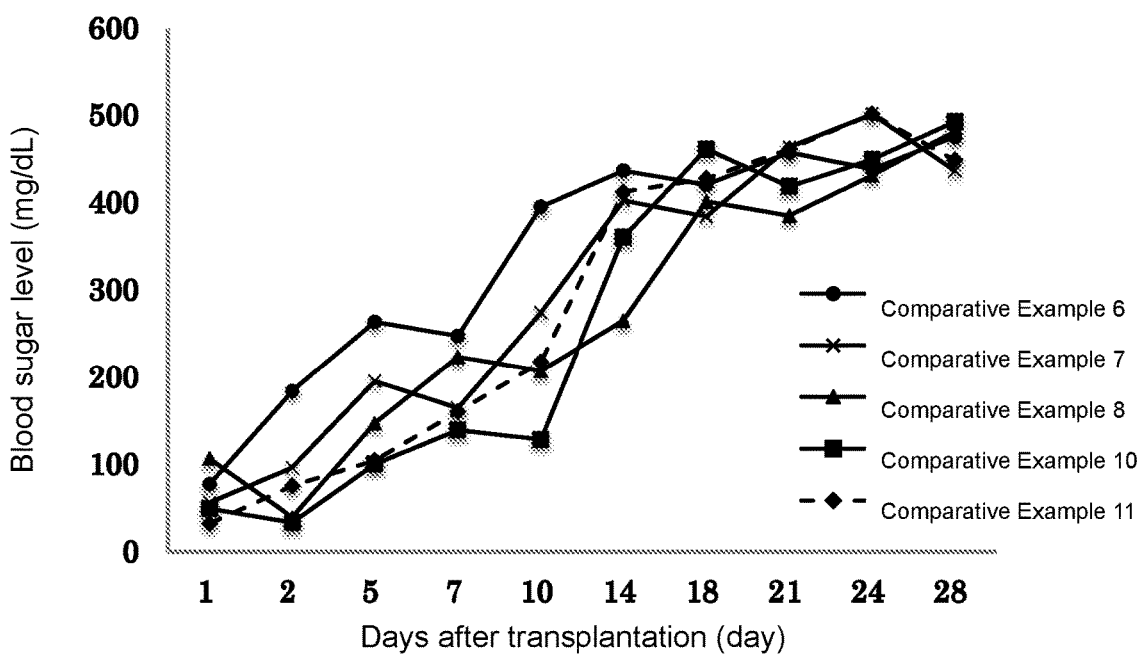
FIG. 3 shows the temporal change of the blood sugar levels of diabetic model animals after transplantation of the frozen and thawed pancreatic islet devices of Comparative Examples 6 to 11.

In the cases of the frozen and thawed bioartificial pancreatic islet devices of Comparative Examples 1 to 18, at the time when the PVA gel was frozen and thawed, the form of the pancreatic islets embedded therein had already collapsed. In an experiment in which the devices were transplanted to diabetic model animals, as shown in FIGS. 2 and 3, although transient decreases in the blood sugar level attributable to graft collapse were observed in some cases, the blood level increased again within 2 weeks after transplantation in all the cases. Thus, the frozen and thawed pancreatic islet devices were proved not to be capable of healing diabetes.

Also, as clearly shown in Table 3, the cell or tissue embedding device of Example 1 and Example 2 of the present invention exhibited a healing effect on diabetes due to the pancreatic islet cells embedded therein while Comparative Examples 1 to 18 did not exhibit any healing effect on diabetes. In Comparative Examples 1 to 18, the pancreatic islet grafts were significantly damaged at the time of transplantation, and therefore, even transplanted into the abdominal cavity known to be the most effective site for the transplantation, did not exhibit any healing effect on diabetes. In contrast, the cell or tissue embedding device of Example 1 and Example 2 of the present invention exhibited a healing effect on diabetes even though the devices were transplanted under the skin known to be the least effective site for the transplantation. These results are noteworthy.

The results of Example 1 and Example 2 show that the immunoisolation capability is retained, and therefore, the activity of the embedded cells is favorably retained. For this reason, it is suggested that even when other cells or living tissue is used as the biological component (C), the effects of retaining the immunoisolation capability and of retaining the activity of embedded cells can be obtained.

Examples 3 to 5

Immunoisolation Capability Verification Test (Complement Penetration Blocking Test)

Aqueous gels were prepared in the same manner as in Example 1 except that the solid concentration in the sol was 6.5% (Example 3), 4.3% (Example 4) and 2.1% (Example 5). To 680 μL of each aqueous gel, 20 μL of pellets of sensitized sheep erythrocytes (Denka Seiken) was added, and mixed therewith, and 170 μL of the mixture was placed in the well of a glass bottom dish (diameter 35 mm, well diameter 12 mm, AGC Techno Glass). Thereon, a PET mesh with a diameter of 15 mm and a PET mesh with a diameter of 22 mm, onto both sides of which meshes the gel had been applied, were placed in this order. After 200 μL of the gel was placed thereon, the dish was left stand at 4° C. for 48 hours. To this, 2.5 mL/dish of a gelatin veronal buffer was added, and after the dish was left stand at 4° C. overnight, the aqueous gel was subjected to the test.

As a control not having a complement penetration blocking effect, a collagen gel group was prepared as follows. To 680 μL of 0.21% collagen (Cellmatrix Type I-A, Nitta Gelatin) containing 5 mM NaOH, 26 mM NaHCO$_3$, 20 mM HEPES, and RPMI 1640, 20 μL of pellets of sensitized sheep erythrocytes was added, and mixed therewith. Of the mixture, 170 μL was placed in the well of a glass bottom dish and left stand at 37° C. for 15 minutes for gelation of the collagen. A PET mesh with a diameter of 15 mm and a PET mesh with a diameter of 22 mm, onto both sides of which meshes a collagen gel had been applied, were placed on the well in this order. After 400 μL of the collagen gel was placed thereon, the dish was left stand at 37° C. for 15 minutes. To this, 2.5 mL/dish of a gelatin veronal buffer was added, and after the dish was left stand at 4° C. overnight, the gel was subjected to the test.

Immediately before the start of the complement penetration blocking test, the buffer was removed from the dishes (2 dishes per group), and 2.5 mL/dish of a gelatin veronal buffer and 100 μL/dish of guinea pig serum (Denka Seiken) or a deactivated (the serum was heated at 57° C. for 30 minutes to deactivate complements) guinea pig serum were added thereto. The dishes were placed in an incubator at 28° C., and after 10 days, 10 μL was taken from each dish. The absorbance at 405 nm of each solution was measured using NanoDrop (Thermo Fisher Scientific Inc.), and the ratio of the serum to the deactivated serum was determined for each Example group and the control group.

The ratio of the serum to the deactivated serum of Examples 3, 4, and 5 were 1.0, 1.47, and 1.69, respectively.

Meanwhile, the ratio of the serum to the deactivated serum of the collagen gel group as the control group was 1.75.

The results show that the ratios of the serum to the deactivated serum of Examples 4 and 5 were lower than the ratio of the control group, demonstrating a mild complement penetration blocking effect. Thus, all of the aqueous gels of Examples 3 to 5 were shown to be capable of blocking the penetration of complements of small sizes and have an immunoisolation capability albeit to different extents. In particular, the ratios of the serum to the deactivated serum of Example 3 was 1.0, showing that the penetration of complements was completely blocked.

Examples 6 to 21

FDA/PI Measurement

The pancreatic islet device having the composition shown in Table 4 prepared in the same manner as in Example 1 was washed twice with 3 mL/well of PBS (room temperature) for 3 minutes each. To 3 mL of PBS in a 6 well plate, 15 μL of a solution of fluorescein diacetate (FDA: Calbiochmem, San Diego, USA) dissolved in acetone (Wako Pure Chemical Industries, Tokyo, Japan) at 5 mg/mL and 20 μL of a solution of propidium iodide (PI: Sigma-Aldrich, St. Louis, Mo., USA) dissolved in distilled water at 0.5 mg/mL were added to give a FDA/PI staining solution. Into this, the washed pancreatic islet device was transferred and stained in the dark for 5 minutes, and then washed with 3 mL of PBS for 3 minutes. The pancreatic islet device was placed on a cover glass (Matsunami Glass Ind., Ltd., Osaka, Japan), and using a fluorescence microscope (BZ-900: KEYENCE, Tokyo, Japan), the localization of FDA (excitation wavelength 470/40 nm, absorption wavelength 525/50) and of PI (excitation wavelength 540/25 nm, absorption wavelength 605/60) in the pancreatic islet was observed.

In the FDA measurement (staining), the presence of living cells were confirmed (FDA (+)), and dead cells were hardly observed for all the Examples. Meanwhile, in the PI measurement, cell nuclei were not stained, revealing that dead cells were hardly present as with the results of FDA staining.

TABLE 4

| Example | Denatured PVA resin (A) | Crosslinking agent (B) | Concentration of denatured PVA resin (A) | Amount of added crosslinking agent (B) | FDA/PI Measurement results |
|---|---|---|---|---|---|
| 6 | Synthetic Example 4 | Synthetic Example 3 | 8 | 10 | +/− |
| 7 | Synthetic Example 5 | Synthetic Example 3 | 6 | 20 | +/− |
| 8 | Synthetic Example 6 | Synthetic Example 3 | 5 | 11 | +/− |

TABLE 4-continued

| Example | Denatured PVA resin (A) | Crosslinking agent (B) | Concentration of denatured PVA resin (A) | Amount of added crosslinking agent (B) | FDA/PI Measurement results |
|---|---|---|---|---|---|
| 9 |  | Synthetic Example 3 | 6 | 11 | +/− |
| 10 | Synthetic Example 7 | Synthetic Example 3 | 4 | 10 | +/− |
| 11 |  | Synthetic Example 3 | 5 | 10 | +/− |
| 12 | Synthetic Example 8 | Synthetic Example 3 | 4 | 15 | +/− |
| 13 |  | Synthetic Example 3 | 5 | 15 | +/− |
| 14 | Synthetic Example 9 | Synthetic Example 3 | 4 | 14 | +/− |
| 15 | Synthetic Example 10 | Synthetic Example 3 | 3 | 13 | +/− |
| 16 |  | Synthetic Example 3 | 4 | 13 | +/− |
| 17 | Synthetic Example 11 | Synthetic Example 3 | 4 | 15 | +/− |
| 18 |  | Synthetic Example 3 | 5 | 15 | +/− |
| 19 | Synthetic Example 1 | ADH | 5 | 7 | +/− |
| 20 | Synthetic Example 10 | Synthetic Example 3 | 5 | 3 | +/− |
| 21 | Synthetic Example 1 | Synthetic Example 3 | 5 | 10 | +/− |

Concentration of denatured PVA resin (A): concentration of denatured PVA resin (A) in the device (w/v %)
Amount of added crosslinking agent (B): amount of crosslinking agent (B) added to denatured PVA resin (A) (w/v %)
ADH: adipic acid dihydrazide
FDA/PI measurement evaluation criteria: FDA: (+) living cells exist, (−) cytoplasm destroyed, PI: (+) cell nucleus destroyed, (−) living cells exist Comparative Example 19

The pancreatic islet device prepared in Comparative Example 1 was subjected to the FDA/PI measurement as in the Examples. In the FDA measurement, no stained image was observed, and in the PI measurement, stained cell nuclei were clearly observed. The results of both the measurements confirmed that the pancreatic islets in the device of the Comparative Example widely became necrotic.

Example 22

Aqueous Gel Solid Concentration and Stress Measurement

A 7% aqueous solution of the PVA denatured with diacetone acrylamide obtained in Synthetic Example 1 and a 10% aqueous solution of the amino polyacrylamide 2 obtained in Synthetic Example 3 were mixed at the concentration of the denatured PVA resin (A) and the added amount of the crosslinking agent (B) shown in Table 5. The mixture was filled into a column vessel 34 mm in diameter and left stand at 20° C. for 24 hours to prepare an aqueous gel having a diameter of 34 mm and a height of 17 mm.

The obtained aqueous gel had a solid concentration of 5.5% and a stress of 4.9 kPa at 20° C.

The solids concentration was measured using a heating-and-drying moisture analyzer (A&D, MS-70). On the sample dish of the moisture analyzer, a glass fiber sheet was placed, and about 1 g of the aqueous gel was allowed to uniformly permeate into the sheet. Then, the solid content of the aqueous gel was measured under the conditions of the sample dish temperature of 120° C. and the measuring time (warming time) of 15 minutes. In the measurement, the moisture analyzer was set in a mode for displaying the solid content (%). The formula for calculating the solid content is mass after drying/mass before drying×100(%).

The stress measurement was performed using a compact table-top tester EZ Test EZ-SX made by Shimadzu Corporation, according to the directions for use. Specifically, the stress of the aqueous gel having a diameter of 34 mm and a height of 17 mm was measured at 20% indentation using a cylinder jig 20 mm in diameter.

Examples 23 to 39

Aqueous gels were prepared as in Example 22 except that the type and the concentration of the PVA resin (A), the type and the added amount of the crosslinking agent (B), etc. were appropriately changed as shown in Table 5, and the solid concentration and the stress were measured.

TABLE 5

| Example | Denatured PVA resin (A) | Crosslinking agent (B) | Concentration of denatured PVA resin (A) | Amount of added crosslinking agent (B) | Left-stand time at 20° C. | Solid concentration (%) | Stress (kPa) |
|---|---|---|---|---|---|---|---|
| 22 | Synthetic Example 1 | Synthetic Example 3 | 5 | 10 | 24 hr | 5.5 | 4.9 |
| 23 | Synthetic Example 1 | Synthetic Example 3 | 5 | 10 | 48 hr | 5.5 | 6.4 |
| 24 | Synthetic Example 1 | Synthetic Example 3 | 5 | 10 | 72 hr | 5.5 | 7.6 |

TABLE 5-continued

| Example | Denatured PVA resin (A) | Crosslinking agent (B) | Concentration of denatured PVA resin (A) | Amount of added crosslinking agent (B) | Left-stand time at 20° C. | Solid concentration (%) | Stress (kPa) |
|---|---|---|---|---|---|---|---|
| 25 | Synthetic Example 1 | Synthetic Example 3 | 5 | 10 | 168 hr | 5.6 | 9.3 |
| 26 | Synthetic Example 1 | Synthetic Example 3 | 3 | 10 | 24 hr | 3.3 | 0.7 |
| 27 | Synthetic Example 1 | Synthetic Example 3 | 3 | 10 | 48 hr | 3.2 | 1.2 |
| 28 | Synthetic Example 1 | Synthetic Example 3 | 3 | 10 | 72 hr | 3.2 | 1.5 |
| 29 | Synthetic Example 1 | Synthetic Example 3 | 3 | 10 | 168 hr | 3.3 | 2.0 |
| 30 | Synthetic Example 7 | Synthetic Example 3 | 10 | 10 | 24 hr | 11.2 | 38.4 |
| 31 | Synthetic Example 7 | Synthetic Example 3 | 10 | 10 | 48 hr | 11.4 | 45.0 |
| 32 | Synthetic Example 7 | Synthetic Example 3 | 10 | 10 | 72 hr | 11.6 | 49.0 |
| 33 | Synthetic Example 7 | Synthetic Example 3 | 10 | 10 | 168 hr | 12.0 | 61.1 |
| 34 | Synthetic Example 6 | Synthetic Example 3 | 12 | 10 | 24 hr | 13.8 | 47.2 |
| 35 | Synthetic Example 6 | Synthetic Example 3 | 12 | 10 | 48 hr | 13.8 | 53.3 |
| 36 | Synthetic Example 6 | Synthetic Example 3 | 12 | 10 | 72 hr | 13.8 | 63.3 |
| 37 | Synthetic Example 6 | Synthetic Example 3 | 12 | 10 | 168 hr | 14.0 | 70.0 |
| 38 | Synthetic Example 5 | ADH | 5 | 10 | 72 hr | 5.5 | 2.2 |
| 39 | Synthetic Example 5 | ADH | 5 | 10 | 168 hr | 5.5 | 2.7 |

Concentration of denatured PVA resin (A): concentration of denatured PVA resin (A) in the device (wt %)
Amount of added crosslinking agent (B): amount of crosslinking agent (B) added to denatured PVA resin (A) (wt %)
ADH: adipic acid dihydrazide

Example 40

Tissue Embedding Device Solid Concentration and Stress measurement

A 7% aqueous solution of the PVA denatured with diacetone acrylamide obtained in Synthetic Example 1, a 10% aqueous solution of the amino polyacrylamide 2 obtained in Synthetic Example 3, and a 10-fold concentration HBSS (Hank's balanced salt solution) were mixed at the concentration of the denatured PVA resin (A), the added amount of the cross linking agent (B), and the added amount of HBSS shown in Table 6. The mixture was filled into a column vessel 34 mm in diameter and left stand at 37° C. for 30 minutes and then at 4° C. for 48 hours to prepare a tissue embedding device having a diameter of 34 mm and a height of 17 mm.

The obtained tissue embedding device had a solid concentration of 6.4% and a stress of 5.3 kPa at 20° C.

The solids concentration was measured using a heating-and-drying moisture analyzer (A&D, MS-70). On the sample dish of the moisture analyzer, a glass fiber sheet was placed, and about 1 g of the tissue embedding device was allowed to uniformly permeate into the sheet. Then, the solid content of the tissue embedding device was measured under the conditions of the sample dish temperature of 120° C. and the measuring time (warming time) of 15 minutes. In the measurement, the moisture analyzer was set in a mode for displaying the solid content (%). The formula for calculating the solid content is mass after drying/mass before drying× 100(%).

The stress measurement was performed using a compact table-top tester EZ Test EZ-SX made by Shimadzu Corporation, according to the directions for use. Specifically, the stress of the tissue embedding device, which is an aqueous gel having a diameter of 34 mm and a height of 17 mm was measured at 20% indentation using a cylinder jig 20 mm in diameter.

Examples 41 to 79

Tissue embedding devices were prepared as in Example 40 except that the type and the concentration of the PVA resin (A), the type and the added amount of the crosslinking agent (B), the amount of HBSS etc. were appropriately changed as shown in Table 6, and the solid concentration and the stress were measured.

TABLE 6

| Example | Denatured PVA resin (A) | Crosslinking agent (B) | Concentration of denatured PVA resin (A) | Amount of added crosslinking agent (B) | Amount of added HBSS | Left-stand time 37° C. | Left-stand time 20° C. | Solid concentration (%) | Stress (kPa) |
|---|---|---|---|---|---|---|---|---|---|
| 40 | Synthetic Example 1 | Synthetic Example 3 | 5 | 10 | 1 | 30 min | 48 hr | 6.4 | 5.3 |

TABLE 6-continued

| Example | Denatured PVA resin (A) | Crosslinking agent (B) | Concentration of denatured PVA resin (A) | Amount of added crosslinking agent (B) | Amount of added HBSS | Left-stand time 37° C. | Left-stand time 20° C. | Solid concentration (%) | Stress (kPa) |
|---|---|---|---|---|---|---|---|---|---|
| 41 | Synthetic Example 1 | Synthetic Example 3 | 5 | 10 | 1 | 100 min | 48 hr | 6.4 | 5.4 |
| 42 | Synthetic Example 1 | Synthetic Example 3 | 5 | 10 | 1 | 180 min | 48 hr | 6.4 | 5.6 |
| 43 | Synthetic Example 1 | Synthetic Example 3 | 5 | 10 | 1 | 24 hr | — | 6.4 | 5.5 |
| 44 | Synthetic Example 1 | Synthetic Example 3 | 3 | 10 | 1 | 100 min | 48 hr | 4.2 | 1.1 |
| 45 | Synthetic Example 1 | Synthetic Example 3 | 3 | 10 | 1 | 210 min | 48 hr | 4.2 | 1.1 |
| 46 | Synthetic Example 1 | Synthetic Example 3 | 3 | 10 | 1 | 24 hr | — | 4.2 | 1.1 |
| 47 | Synthetic Example 6 | Synthetic Example 3 | 6 | 11 | 1 | 100 min | 48 hr | 7.6 | 7.3 |
| 48 | Synthetic Example 6 | Synthetic Example 3 | 6 | 11 | 1 | 180 min | 48 hr | 7.6 | 7.5 |
| 49 | Synthetic Example 6 | Synthetic Example 3 | 6 | 11 | 1 | 24 hr | — | 7.6 | 6.1 |
| 50 | Synthetic Example 6 | Synthetic Example 3 | 4 | 11 | 1 | 100 min | 48 hr | 5.4 | 1.5 |
| 51 | Synthetic Example 6 | Synthetic Example 3 | 4 | 11 | 1 | 300 min | 48 hr | 5.3 | 1.7 |
| 52 | Synthetic Example 6 | Synthetic Example 3 | 4 | 11 | 1 | 24 hr | — | 5.3 | 1.5 |
| 53 | Synthetic Example 5 | Synthetic Example 3 | 6 | 20 | 1 | 60 min | 48 hr | 10.8 | 40.4 |
| 54 | Synthetic Example 5 | Synthetic Example 3 | 6 | 20 | 1 | 120 min | 48 hr | 10.4 | 44 |
| 55 | Synthetic Example 5 | Synthetic Example 3 | 6 | 20 | 1 | 180 min | 48 hr | 10 | 47.7 |
| 56 | Synthetic Example 5 | Synthetic Example 3 | 6 | 15 | 1 | 60 min | 48 hr | 7.7 | 21.4 |
| 57 | Synthetic Example 5 | Synthetic Example 3 | 6 | 15 | 1 | 120 min | 48 hr | 8.2 | 18.2 |
| 58 | Synthetic Example 5 | Synthetic Example 3 | 6 | 15 | 1 | 180 min | 48 hr | 8 | 19.2 |
| 59 | Synthetic Example 5 | Synthetic Example 3 | 7.5 | 15 | 1 | 60 min | 48 hr | 10.7 | 48.8 |
| 60 | Synthetic Example 5 | Synthetic Example 3 | 7.5 | 15 | 1 | 120 min | 48 hr | 10.6 | 44.1 |
| 61 | Synthetic Example 5 | Synthetic Example 3 | 7.5 | 15 | 1 | 180 min | 48 hr | 10.4 | 44.7 |
| 62 | Synthetic Example 7 | Synthetic Example 3 | 5 | 10 | 1 | 140 min | 48 hr | 6.5 | 6 |
| 63 | Synthetic Example 7 | Synthetic Example 3 | 5 | 10 | 1 | 300 min | 48 hr | 6.4 | 6.4 |
| 64 | Synthetic Example 7 | Synthetic Example 3 | 3 | 10 | 1 | 120 min | 48 hr | 4.2 | 1.2 |
| 65 | Synthetic Example 7 | Synthetic Example 3 | 3 | 10 | 1 | 280 min | 48 hr | 4.2 | 1.2 |
| 66 | Synthetic Example 7 | Synthetic Example 3 | 10 | 10 | 1 | 60 min | 48 hr | 12.3 | 43.2 |
| 67 | Synthetic Example 7 | Synthetic Example 3 | 10 | 10 | 1 | 180 min | 48 hr | 12 | 38.9 |
| 68 | Synthetic Example 8 | Synthetic Example 3 | 15 | 5 | 1 | 120 min | 48 hr | 6.3 | 8.9 |
| 69 | Synthetic Example 8 | Synthetic Example 3 | 15 | 5 | 1 | 180 min | 48 hr | 6.4 | 11.4 |
| 70 | Synthetic Example 8 | Synthetic Example 3 | 15 | 4 | 1 | 140 min | 48 hr | 5.2 | 5.4 |
| 71 | Synthetic Example 8 | Synthetic Example 3 | 15 | 4 | 1 | 300 min | 48 hr | 5.2 | 5.4 |
| 72 | Synthetic Example 10 | Synthetic Example 3 | 10 | 5 | 1 | 60 min | 48 hr | 10.3 | 5.8 |
| 73 | Synthetic Example 10 | Synthetic Example 3 | 10 | 5 | 1 | 120 min | 48 hr | 10.9 | 5.8 |
| 74 | Synthetic Example 10 | Synthetic Example 3 | 10 | 3 | 1 | 120 min | 48 hr | 4.3 | 2.1 |
| 75 | Synthetic Example 10 | Synthetic Example 3 | 10 | 3 | 1 | 240 min | 48 hr | 4.3 | 2.5 |
| 76 | Synthetic Example 9 | Synthetic Example 3 | 10 | 5 | 1 | 60 min | 48 hr | 9 | 6.4 |
| 77 | Synthetic Example 9 | Synthetic Example 3 | 10 | 5 | 1 | 180 min | 48 hr | 9.4 | 6.5 |

TABLE 6-continued

| Example | Denatured PVA resin (A) | Crosslinking agent (B) | Concentration of denatured PVA resin (A) | Amount of added crosslinking agent (B) | Amount of added HBSS | Left-stand time 37° C. | Left-stand time 20° C. | Solid concentration (%) | Stress (kPa) |
|---|---|---|---|---|---|---|---|---|---|
| 78 | Synthetic Example 9 | Synthetic Example 3 | 10 | 3 | 1 | 180 min | 48 hr | 3.9 | 1.8 |
| 79 | Synthetic Example 9 | Synthetic Example 3 | 10 | 3 | 1 | 300 min | 48 hr | 3.9 | 1.9 |

Concentration of denatured PVA resin (A): concentration of denatured PVA resin (A) in the device (wt %)
Amount of added crosslinking agent (B): amount of crosslinking agent (B) added to denatured PVA resin (A) (wt %)
Amount of added HBSS: concentration of Hanks' balanced salt solution in the liquid mixture (wt %)

INDUSTRIAL APPLICABILITY

According to the present invention, an aqueous gel capable of retaining its strong structure in pH and temperature conditions less harmful to embedded living cells or living tissue can easily be formed using less toxic components, and therefore, a cell or tissue embedding device which is highly capable of supplying a physiologically active substance, such as a hormone or a protein, useful for a patient and which isolates contained cells or tissue from the biological defense mechanism can be provided.

The invention claimed is:

1. A cell or tissue embedding device having an aqueous gel serving as an immunoisolation layer, the aqueous gel containing, as components thereof, a denatured polyvinyl alcohol resin having an activated carbonyl group and a crosslinking agent wherein the device is a macrocapsule device comprising a cell or tissue, wherein the device is configured to be implanted in a subject, and wherein the denatured polyvinyl alcohol resin comprises a 4 mass % aqueous solution having a viscosity from 53.4 to 500 mPa·s, and wherein the cells or tissue are not from living microorganisms.

2. The cell or tissue embedding device according to claim 1, wherein the aqueous gel has a gelation at a temperature of 0-60° C.

3. The cell or tissue embedding device according to claim 1, wherein the aqueous gel has a stress of 0.5 to 100 kPa.

4. The cell or tissue embedding device according to claim 1, wherein the denatured polyvinyl alcohol resin having an activated carbonyl group is diacetone acrylamide-denatured polyvinyl alcohol.

5. The cell or tissue embedding device according to claim 4, wherein the diacetone acrylamide-denatured polyvinyl alcohol contains 0.5 to 15 mol % diacetone acrylamide unit relative to the whole denatured polyvinyl alcohol.

6. The cell or tissue embedding device according to claim 1, wherein the crosslinking agent is adipic acid dihydrazide or aminopolyacrylamide.

7. The cell or tissue embedding device according to claim 1, wherein a biological component and a cell culture component are embedded in the immunoisolation layer.

8. The cell or tissue embedding device according to claim 7, wherein the biological component is one or more selected from the group consisting of pancreatic islet cells, pancreatic ductal cells, liver cells, nerve cells, thyroid cells, parathyroid cells, kidney cells, adrenal cells, pituitary cells, splenic cells, fat cells, bone marrow cells, mesenchymal stem cells, embryonic stem (ES) cells, and induced pluripotent stem (iPs) cells.

9. The cell or tissue embedding device according to the claim 7, wherein the biological component is pancreatic islet cells or liver cells.

10. The cell or tissue embedding device according to claim 7, wherein the cell culture component is an acetate or phosphate buffer containing one or more selected from the group consisting of Na, K, Cl, Ca, and glucose.

11. The cell or tissue embedding device according to claim 1, having a stress of 0.5 to 100 kPa.

12. The cell or tissue embedding device according to claim 1, comprising a supporting base.

13. The cell or tissue embedding device according to claim 12, wherein the material of the supporting base is one or more selected from the group consisting of polyethylene terephthalate (PET), polyethylene (PE), polypropylene (PP) Teflon, and metal.

14. The cell or tissue embedding device according to claim 1, wherein the device comprises pancreatic islet cells.

15. The cell or tissue embedding device according to claim 14, wherein the device is implanted into a subject, and wherein a blood sugar level is reduced by greater than 50% in the subject immediately after the device is implanted and the blood sugar level is reduced by greater than 50% for at least 6 months after the device is implanted in the subject.

16. The cell or tissue embedding device according to claim 1, wherein the device comprises a cell culture medium.

17. The cell or tissue embedding device according to claim 15, wherein the device comprises from 1,000 to 100,000 pancreatic islet cells per cubic millimeter of the gel device embedding space.

18. The cell or tissue embedding device according to claim 15, wherein the device comprises from 1,000 to 1,000,000 pancreatic islet cells per kilogram of body weight of the subject.

19. The cell or tissue embedding device according to claim 15, wherein the aqueous gel comprises from about 2 wt % to about 10 wt % of the denatured polyvinyl alcohol resin by volume of the gel and from about 0.2 wt % to about 1.0 wt % of the crosslinking agent by volume of the gel.

* * * * *

UNITED STATES PATENT AND TRADEMARK OFFICE
CERTIFICATE OF CORRECTION

PATENT NO. : 11,684,693 B2
APPLICATION NO. : 16/487400
DATED : June 27, 2023
INVENTOR(S) : Akinobu Oharuda It is certified that error appears in the above-identified patent and that said Letters Patent is hereby corrected as shown below:

On the Title Page

Column 1, Line 1, under Title, after "DEVICE" insert --HAVING AN AQUEOUS PVA GEL SERVING AS AN IMMUNOISOLATION LAYER--.

Column 2, Line 5, under Other Publications, delete "(viny1" and insert --(vinyl--.

Column 2, Line 8, under Other Publications, delete "titel:" and insert --title:--.

In the Specification

In Column 1, Line 1, after "DEVICE" insert --HAVING AN AQUEOUS PVA GEL SERVING AS AN IMMUNOISOLATION LAYER--.

In Column 2, Line 37, delete "2356" and insert --2356.--.

In Column 8, Line 57, delete "5-ethyl vinylpyridine," and insert --5-ethyl-2-vinylpyridine,--.

In Column 10, Line 50, delete "hydrazinocarbonoethyl" and insert --hydrazinocarbono ethyl--.

In Column 10, Line 59, delete "biuretry-tri" and insert --biuretry tri--.

In Column 20, Lines 7-8, delete "Crigler Najjar" and insert --Crigler-Najjar--.

In Column 28, Line 35, delete "Calbiochmem," and insert --Calbiochem,--.

In the Claims

In Column 35, Claim 2, Line 40, delete "0-60° C." and insert --0 to 60° C.--.

Signed and Sealed this
Twenty-sixth Day of December, 2023

Katherine Kelly Vidal
*Director of the United States Patent and Trademark Office*